United States Patent
Ding et al.

(10) Patent No.: US 11,547,797 B2
(45) Date of Patent: Jan. 10, 2023

(54) MEDICAL SYRINGE SYSTEM WITH FILTERED FILLING PORT

(71) Applicants: BAXTER INTERNATIONAL INC., Deerfield, IL (US); BAXTER HEALTHCARE SA, Glattpark (CH)

(72) Inventors: Yuanpang Samuel Ding, Long Grove, IL (US); Marc Steven Minkus, Linconshire, IL (US); Ying-Cheng Lo, Long Grove, IL (US); Mark Joseph Doty, Grayslake, IL (US); Thomas Edward Dudar, Palatine, IL (US); Grant Anthony Bomgaars, Kildeer, IL (US); Mark Edward Pasmore, Grayslake, IL (US); Michael Joseph Sadowski, Ringwood, IL (US); Anastasios Hristakos, Evanston, IL (US); Bernd Krause, Rangendingen (DE); Joseph Vincent Ranalletta, Greenville, SC (US)

(73) Assignees: BAXTER INTERNATIONAL INC., Deerfield, IL (US); BAXTER HEALTHCARE SA, Glattpark (CH)

(*) Notice: Subject to any disclaimer, the term of this patent is extended or adjusted under 35 U.S.C. 154(b) by 484 days.

(21) Appl. No.: 16/631,051

(22) PCT Filed: Jul. 12, 2018

(86) PCT No.: PCT/US2018/041811
§ 371 (c)(1),
(2) Date: Jan. 14, 2020

(87) PCT Pub. No.: WO2019/018203
PCT Pub. Date: Jan. 24, 2019

(65) Prior Publication Data
US 2020/0147310 A1     May 14, 2020

Related U.S. Application Data

(60) Provisional application No. 62/533,440, filed on Jul. 17, 2017.

(51) Int. Cl.
*A61M 5/165* (2006.01)
*A61J 1/20* (2006.01)
(Continued)

(52) U.S. Cl.
CPC ............ *A61M 5/165* (2013.01); *A61J 1/2086* (2015.05); *A61M 5/1407* (2013.01);
(Continued)

(58) Field of Classification Search
CPC ................ A61M 5/165; A61M 5/3145; A61M 2005/1657
See application file for complete search history.

(56) References Cited

U.S. PATENT DOCUMENTS

| | | | | |
|---|---|---|---|---|
| 5,080,649 A * | 1/1992 | Vetter | ............... | A61M 5/31596 604/91 |
| 2008/0294100 A1* | 11/2008 | de Costa | ............. | A61M 5/3293 424/463 |
| 2015/0283032 A1* | 10/2015 | Lin | .......................... | A61M 5/38 604/406 |

FOREIGN PATENT DOCUMENTS

| CN | 200951242 Y | 9/2007 |
|---|---|---|
| EP | 2830683 A1 | 2/2015 |

(Continued)

OTHER PUBLICATIONS

International Search Report for International Application No. PCT/US2018/0R1811, dated Nov. 19, 2018.
(Continued)

*Primary Examiner* — Jenna Zhang
(74) *Attorney, Agent, or Firm* — Marshall, Gerstein & Borun LLP

(57) ABSTRACT

A syringe system includes a syringe and a filtration device connected to the syringe for sterilizing and introducing fluid into the syringe. The syringe includes a syringe barrel having a proximal end defining a barrel opening, a distal end defining a delivery opening, a bore extending between the proximal end and the distal end, and a stopper disposed in the bore of the syringe barrel. The filtration device has an inlet and an outlet coupled in fluid communication with the delivery opening at the distal end of the syringe barrel. The
(Continued)

filtration device includes a stem and a filter membrane disposed in line with the stem. The filter membrane optionally has a plurality of pores each with a nominal pore size in a range of approximately 0.1 μm to approximately 0.5 μm such that a pharmaceutical fluid can be introduced as a sterilized pharmaceutical fluid into the bore of the syringe barrel by passing through the filtration device.

12 Claims, 14 Drawing Sheets

(51) Int. Cl.
*A61M 5/178* (2006.01)
*A61M 5/31* (2006.01)
*A61M 5/14* (2006.01)

(52) U.S. Cl.
CPC ........ *A61M 5/1409* (2013.01); *A61M 5/1782* (2013.01); *A61M 5/3145* (2013.01); *A61M 2005/1657* (2013.01); *A61M 2205/705* (2013.01)

(56) References Cited

FOREIGN PATENT DOCUMENTS

| WO | WO-2007089309 A2 | 8/2007 |
| WO | WO-2016131463 A1 | 8/2016 |

OTHER PUBLICATIONS

Written Opinion for International Application No. PCT/US2018/0R1811, dated Nov. 19, 2018.

* cited by examiner

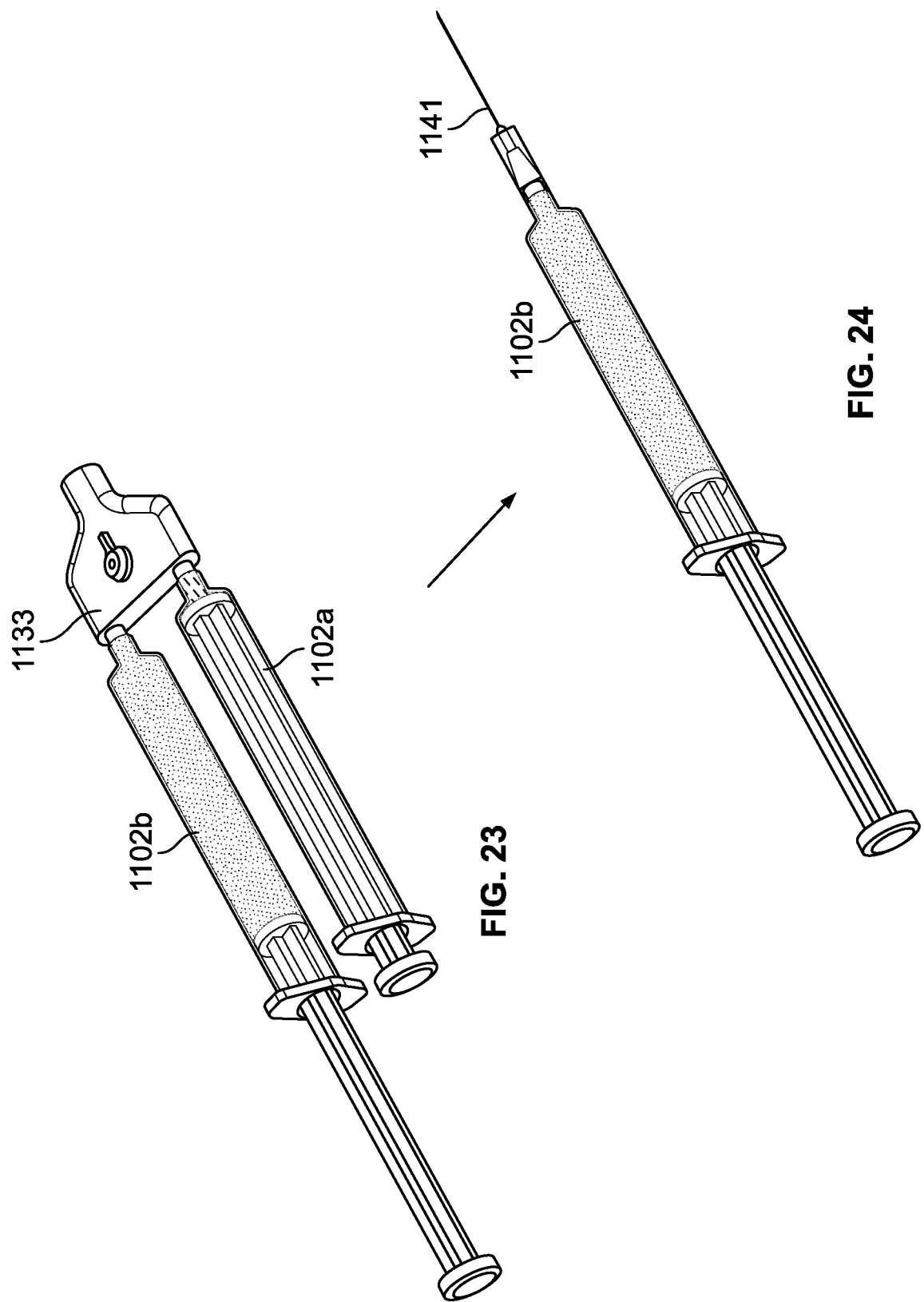

MEDICAL SYRINGE SYSTEM WITH FILTERED FILLING PORT

CROSS REFERENCE TO AND RELATED APPLICATIONS

This is the United States national phase of PCT/US18/41811, filed Jul. 12, 2018, which claims the priority benefit of U.S. Provisional Application Ser. No. 62/533,440, filed Jul. 17, 2017, the entire contents of each of which are incorporated herein by reference.

Additionally, the following related and co-owned U.S. applications are expressly incorporated herein by reference in their entirety: U.S. Provisional Patent Application Ser. No. 62/533,362, (entitled STERILE PRODUCT BAG WITH FILTERED PORT); U.S. Provisional Patent Application Ser. No. 62/533,380, (entitled DUAL CONTAINER SYSTEM FOR PRODUCT RECONSTITUTION); U.S. Provisional Patent Application Ser. No. 62/533,408, (entitled MEDICAL PRODUCT INCLUDING PRE-FILLED PRODUCT BAG WITH FILTERED FLUID PORT); and U.S. Provisional Patent Application Ser. No. 62/533,427, (entitled FILTERED PRODUCT BAG WITH COMPACT FORM FACTOR), each filed on Jul. 17, 2017.

FIELD OF THE DISCLOSURE

This disclosure relates to a medical syringe and, in particular, a medical syringe system for reconstituting and administering a sterile medicament or nutritional product to a patient.

BACKGROUND

Often, drugs and nutrients are mixed with a diluent before being delivered to a patient. The diluent may be, for example, a dextrose solution, a saline solution or even water. Many such drugs or nutrients are supplied in a concentrated form such as powder, liquid, gel, foam, etc., and packaged in glass or plastic vials.

In order for the concentrate to be administered to a patient, it must first undergo reconstitution. As used herein, the term reconstitution includes not only liquidization of non-liquid concentrates but also dilution of liquid concentrates.

One way of reconstituting a concentrate is first to inject a diluent into the vial holding the concentrate. This may typically be performed by a pre-filled syringe having a liquid diluent contained in the syringe barrel. After the rubber stopper of the vial is pierced by the syringe needle, the liquid is injected into the vial. The vial is shaken to reconstitute and dilute the concentrate with the liquid. The liquid is then withdrawn back into the syringe. These steps may be repeated several times to ensure complete reconstitution of the concentrate. After the final mixing, the syringe is withdrawn and the reconstituted medication may then be injected into an administration set for bolus intravenous administration to a patient or into the medication port of a parenteral solution container (e.g., an IV bag) containing a medical solution or diluent such as dextrose or saline solution. The drug, now further diluted with the medical solution in the parenteral solution container, is delivered through an administration set for intravenous administration to the patient. Other methods of administration to the patient may also include attaching a needle to the syringe and proceeding with a venous, intramuscular or subcutaneous injection.

In other embodiments, the concentrate may already be present in the syringe in a lyophilized or other concentrated form. Diluent is then added to the syringe and the reconstitution may take place within the syringe barrel. The syringe assembly may be construed where it contains a single chamber or there may be dual chambers where the diluent is added to one of the chambers with the concentrate contained in the other and the assembly provides for mixing of the components of the chamber.

If the syringe is pre-filled with the container, the sterility is provided by steam or heat sterilizing the syringe after filling with the diluent. The high temperatures present in the sterilization cycle will limit the materials that may be used for the barrel and stopper and may impact the frictional forces between the barrel and stopper. The pre-filled syringe may also cause the syringe to have a shelf life that must be monitored to insure the syringe is used before the expiration of the shelf life. If diluent is added to the syringe, the addition will likely be made by a health care provider using aseptic technique such as connecting the syringe to a container of diluent under a hood. Failure to practice such technique may cause the diluent to contain contaminants and impact sterility.

SUMMARY

One aspect of the present disclosure is directed to a syringe system that includes a syringe and a filtration device connected to the syringe for sterilizing and introducing fluid into the syringe. The syringe includes a syringe barrel having a proximal end defining a barrel opening, a distal end defining a delivery opening, a bore extending between the proximal end and the distal end, and a stopper disposed in the bore of the syringe barrel. The filtration device has an inlet and an outlet coupled in fluid communication with the delivery opening at the distal end of the syringe barrel. The filtration device includes a stem and a filter membrane disposed in line with the stem. The filter membrane optionally has a plurality of pores each with a nominal pore size in a range of approximately 0.1 µm to approximately 0.5 µm such that a pharmaceutical fluid can be introduced as a sterilized pharmaceutical fluid into the bore of the syringe barrel by passing through the filtration device.

In some aspects, the system further includes a port tube connected between the filter membrane and the distal end of the syringe barrel.

In some aspects, the system further includes a valve disposed between the filtration device and the distal end of the syringe barrel.

In some aspects, the valve comprises a three-way valve with a first port operably coupled to the filtration device, a second port operably coupled to the delivery opening of the syringe barrel, and a third port operably coupled to a diverter tube, wherein the three-way valve is movable between a first configuration and a second configuration, such that in the first configuration, the second port fluidly communicates with the first port but not the third port, thereby enabling the pharmaceutical fluid to be introduced into the syringe barrel through the filtration device, and in the second configuration, the second port fluidly communicates with the third port but not the first port, thereby enabling the pharmaceutical fluid to move out of the syringe barrel and to the diverter tube.

In some aspects, the system further includes a product concentrate disposed in the bore of the syringe barrel between the stopper and the distal end.

In some aspects, the bore of the syringe barrel comprises a first chamber and a second chamber separated by a dual-chamber stopper, the first chamber disposed between the proximal end of the syringe barrel and the dual-chamber stopper and the second chamber disposed between the dual-chamber stopper and the distal end of the syringe barrel.

In some aspects, the system further includes a product concentrate disposed in the first chamber.

In some aspects, the syringe comprises a first syringe and the system further comprises a second syringe, the second syringe comprising a syringe barrel having a proximal end defining a barrel opening, a distal end defining a delivery opening, a bore extending between the proximal end and the distal end, and a stopper disposed in the bore, the distal end of the syringe barrel of the second syringe being coupled in fluid communication with the diverter tube for receiving pharmaceutical fluid from the first syringe.

In some aspects, the valve comprises a first valve and the system further comprises a second valve disposed between the diverter tube and the distal end of the syringe barrel of the second syringe.

In some aspects, the second valve comprises a three-way valve with a first port operably coupled to the diverter tube, a second port operably coupled to the delivery opening of the syringe barrel of the second syringe, and a third port operably coupled to an administration tube, wherein the three-way valve is movable between a first configuration and a second configuration, such that in the first configuration, the second port fluidly communicates with the first port but not the third port, thereby enabling the pharmaceutical fluid to be introduced into the syringe barrel of the second syringe from the diverter tube, and in the second configuration, the second port fluidly communicates with the third port but not the first port, thereby enabling the pharmaceutical fluid to move out of the syringe barrel of the second syringe and to the administration tube.

In some aspects, the valve comprises a three-way valve and wherein the syringe comprises a first syringe and the system further comprises a second syringe, the second syringe comprising a syringe barrel having a proximal end defining a barrel opening, a distal end defining a delivery opening, a bore extending between the proximal end and the distal end, and a stopper disposed in the bore, the three-way valve comprising a first port operably coupled to the filtration device, a second port operably coupled to the delivery opening of the first syringe, and a third port operably coupled to the delivery opening of the second syringe, wherein the three-way valve is movable between a first configuration and a second configuration, such that in the first configuration, the second port fluidly communicates with the first port but not the third port, thereby enabling the pharmaceutical fluid to be introduced into the first syringe through the filtration device, and in the second configuration, the second port fluidly communicates with the third port, thereby enabling the pharmaceutical fluid to move out of the first syringe and to the second syringe.

In some aspects, the system further includes a product concentrate disposed in the bore of the syringe barrel of the second syringe at a location between the stopper and the distal end.

In some aspects, the bore of the syringe barrel of the first syringe is empty until receiving the sterilized pharmaceutical fluid from the filtration device.

In some aspects, the filter membrane is shaped as (a) a hollow fiber with an outlet end, an inlet end, and a wall, wherein the pores reside in the wall, or (b) a flat filter disposed within a rectangular, square or box-like filter housing, the flat filter having a wall and pores residing in the wall.

In some aspects, the outlet end of the hollow fiber of the filter membrane is sealed and the inlet end is an open inlet.

In some aspects, the filter membrane is disposed inside of the stem between the inlet and outlet ends.

In some aspects, the filter membrane comprises a plurality of filter membranes

In some aspects, the filter membrane has a wall thickness in the range of approximately 150 µm to approximately 500 µm.

In some aspects, the filter membrane has a longitudinal dimension in the range of approximately 3 cm to approximately 420 cm, an inner diameter in the range of approximately 2 mm to approximately 4 mm, and an outer diameter in the range of approximately 2.3 mm to approximately 5 mm.

In some aspects, the filter membrane is made of at least one of the following materials: a polyolefin, polyvinylidene fluoride, polymethylmethacrylate, polyacrylonitrile, polysulfone, polyethersulfone, and a polymer containing cationic charges.

In some aspects, the stem is one of a flexible stem or a rigid stem.

In some aspects, the stem is made of at least one of the following materials: PVC, PET, a poly(meth)acrylate, a polycarbonate, a polyolefin, a cycloolefin copolymer, polystyrene, or a silicone polymer.

In some aspects, the filtration includes at least one U-shaped hollow fiber filter membrane secured in a U-shaped configuration by a filter membrane housing contained within a filter body.

In some aspects, the filtration device includes a plurality of U-shaped hollow fiber filter membranes.

In some aspects, the filtration device comprises a plurality of parallel hollow fiber membrane filters secured in a side-by-side configuration.

In some aspects, the filtration device comprises a plurality of parallel hollow fiber membrane filters arranged in a circular pattern.

In some aspects, the filter membrane has a nominal pore size in a range of approximately 0.1 µm to approximately 0.22 µm.

Another aspect of the disclosure provides a syringe system including a first syringe, a second syringe, a filtration device, and a first valve. The first syringe comprises a syringe barrel having a proximal end defining a barrel opening, a distal end defining a delivery opening, a bore extending between the proximal end and the distal end, and a stopper disposed in the bore of the syringe barrel. The second syringe comprises a syringe barrel having a proximal end defining a barrel opening, a distal end defining a delivery opening, a bore extending between the proximal end and the distal end, and a stopper disposed in the bore. The filtration device has an inlet and an outlet, the outlet coupled in fluid communication with the delivery opening at the distal end of the first syringe. The filtration device optionally comprising a stem and a filter membrane disposed in line with the stem, the filter membrane having a plurality of pores each with a nominal pore size in a range of approximately 0.1 µm to approximately 0.5 µm such that a pharmaceutical fluid can be introduced as a sterilized pharmaceutical fluid into the bore of the first syringe by passing through the filtration device. The valving arrangement is disposed between the filtration device and the distal end of the first syringe, the valving arrangement for selectively controlling fluid communication between the filtration device and the first syringe and between the first syringe and the second syringe.

In some aspects, the valving arrangement includes a iverter tube fluidly connected between the delivery openings of the first and second syringes such that sterilized fluid can be delivered to the second syringe from the first syringe.

In some aspects, the first valve comprises a three-way valve with a first port operably coupled to the filtration device, a second port operably coupled to the delivery opening of the syringe barrel, and a third port operably coupled to a diverter tube, wherein the three-way valve is movable between a first configuration and a second configuration, such that in the first configuration, the second port fluidly communicates with the first port but not the third port, thereby enabling the pharmaceutical fluid to be introduced into the first syringe through the filtration device, and in the second configuration, the second port fluidly communicates with the third port but not the first port, thereby enabling the pharmaceutical fluid to move out of the first syringe to the diverter tube and second syringe.

In some aspects, the system further comprises a second valve disposed between the diverter tube and the distal end of the syringe barrel of the second syringe.

In some aspects, the second valve comprises a three-way valve with a first port operably coupled to the diverter tube, a second port operably coupled to the delivery opening of the syringe barrel of the second syringe, and a third port operably coupled to an administration tube, wherein the three-way valve is movable between a first configuration and a second configuration, such that in the first configuration, the second port fluidly communicates with the first port but not the third port, thereby enabling the pharmaceutical fluid to be introduced into the syringe barrel of the second syringe from the diverter tube, and in the second configuration, the second port fluidly communicates with the third port but not the first port, thereby enabling the pharmaceutical fluid to move out of the syringe barrel of the second syringe and to the administration tube.

In some aspects, the valving arrangement comprises a three-way valve, the three-way valve comprising a first port operably coupled to the filtration device, a second port operably coupled to the delivery opening of the first syringe, and a third port operably coupled to the delivery opening of the second syringe, wherein the three-way valve is movable between a first configuration and a second configuration, such that in the first configuration, the second port fluidly communicates with the first port but not the third port, thereby enabling the pharmaceutical fluid to be introduced into the first syringe through the filtration device, and in the second configuration, the second port fluidly communicates with the third port, thereby enabling the pharmaceutical fluid to move out of the first syringe and to the second syringe.

In some aspects, the system further comprises a product concentrate disposed in the bore of the syringe barrel of the second syringe.

In some aspects, the bore of the first syringe is empty until receiving the sterilized pharmaceutical fluid from the filtration device.

In some aspects, the system further comprises a port tube connected between the filter membrane and the valving arrangement.

In some aspects, the filter membrane is shaped as a hollow fiber with an outlet end, an inlet end, and a wall, wherein the pores reside in the wall.

In some aspects, the outlet end of the hollow fiber of the filter membrane is sealed and the inlet end is an open inlet.

In some aspects, the filter membrane is disposed inside of the stem between the inlet and outlet ends.

In some aspects, the filter membrane comprises a plurality of filter membranes

In some aspects, the filter membrane has a wall thickness in the range of approximately 150 µm to approximately 500 µm.

In some aspects, the filter membrane has a longitudinal dimension in the range of approximately 3 cm to approximately 420 cm, an inner diameter in the range of approximately 2 mm to approximately 4 mm, and an outer diameter in the range of approximately 2.3 mm to approximately 5 mm.

In some aspects, the filter membrane is made of at least one of the following materials: a polyolefin, polyvinylidene fluoride, polymethylmethacrylate, polyacrylonitrile, polysulfone, polyethersulfone, and a polymer containing cationic charges.

In some aspects, the stem is one of a flexible stem or a rigid stem.

In some aspects, the stem is made of at least one of the following materials: PVC, PET, a poly(meth)acrylate, a polycarbonate, a polyolefin, a cycloolefin copolymer, polystyrene, or a silicone polymer.

In some aspects, the filtration includes at least one U-shaped hollow fiber filter membrane secured in a U-shaped configuration by a filter membrane housing contained within a filter body.

In some aspects, the filtration device includes a plurality of U-shaped hollow fiber filter membranes.

In some aspects, the filtration device comprises a plurality of parallel hollow fiber membrane filters secured in a side-by-side configuration.

In some aspects, the filtration device comprises a plurality of parallel hollow fiber membrane filters arranged in a circular pattern.

In some aspects, the filter membrane has a nominal pore size in a range of approximately 0.1 µm to approximately 0.22 µm.

Yet another aspect of the present disclosure provides a method of reconstituting a medicinal or nutritional product. The method includes providing a syringe comprising a syringe barrel having a proximal end defining a barrel opening, a distal end defining a delivery opening, a bore extending between the proximal end and the distal end, a stopper disposed in the bore of the syringe barrel, and a product concentrate disposed in the bore between the stopper and the distal end. The method also includes connecting an outlet of a filtration device to the delivery opening of the syringe barrel, the filtration device comprising a stem and a filter membrane disposed in line with the stem, the filter membrane optionally having a plurality of pores each with a nominal pore size in a range of approximately 0.1 µm to approximately 0.5 µm. The method also includes introducing a pharmaceutical fluid into the bore of the syringe barrel through the filter membrane such that a sterilized pharmaceutical fluid can be mixed with the product concentrate in the bore.

In some aspects, introducing the pharmaceutical fluid into the bore of the syringe barrel through the filter membrane comprises introducing the pharmaceutical fluid through a plurality of filter membranes.

In some aspects, introducing the pharmaceutical fluid into the bore of the syringe barrel comprises introducing the pharmaceutical fluid through an open outlet end and a sealed outlet end of a hollow fiber of the filter membrane.

In some aspects, introducing the pharmaceutical fluid into the bore of the syringe barrel comprises introducing the pharmaceutical fluid through a filter membrane having a wall thickness in the range of approximately 150 μm to approximately 500 μm.

In some aspects, introducing the pharmaceutical fluid into the bore of the syringe barrel comprises introducing the pharmaceutical fluid through a filter membrane having a longitudinal dimension in the range of approximately 3 cm to approximately 420 cm, an inner diameter in the range of approximately 2 mm to approximately 4 mm, and an outer diameter in the range of approximately 2.3 mm to approximately 5 mm.

In some aspects, introducing the pharmaceutical fluid into the bore of the syringe barrel comprises introducing the pharmaceutical fluid through a filter membrane made of at least one of the following materials: a polyolefin, polyvinylidene fluoride, polymethylmethacrylate, polyacrylonitrile, polysulfone, polyethersulfone, and a polymer containing cationic charges.

In some aspects, introducing the pharmaceutical fluid into the bore of the syringe barrel comprises introducing the pharmaceutical through a filter membrane having at least one U-shaped hollow fiber filter membrane secured in a U-shaped configuration by a filter membrane housing contained within a filter body.

In some aspects, introducing the pharmaceutical through a filter membrane having at least one U-shaped hollow fiber filter membrane comprises introducing pharmaceutical fluid through a plurality of U-shaped hollow fiber filter membranes.

In some aspects, introducing the pharmaceutical fluid into the bore of the syringe barrel comprises introducing the pharmaceutical fluid through a plurality of parallel hollow fiber membrane filters secured in a side-by-side configuration.

In some aspects, introducing the pharmaceutical fluid into the bore of the syringe barrel comprises introducing the pharmaceutical fluid through a plurality of parallel hollow fiber membrane filters arranged in a circular pattern.

In some aspects, introducing the pharmaceutical fluid into the bore of the syringe barrel comprises introducing the pharmaceutical fluid through a filter membrane having a nominal pore size in a range of approximately 0.1 μm to approximately 0.22 μm.

In some aspects, introducing the pharmaceutical fluid into the bore of the syringe barrel comprises introducing the pharmaceutical fluid into a second chamber of the bore which is isolated from a first chamber of the bore by a dual-chamber stopper, the second chamber disposed between the dual-chamber stopper and the distal end of the syringe and the first chamber disposed between the dual-chamber stopper and the proximal end of the syringe.

In some aspects, introducing the product concentrate into the bore of the syringe barrel comprises introducing the product concentrate into the first chamber of the bore.

In some aspects, the method further includes moving the dual-chamber stopper to open a fluid path between the first and second chambers of the bore to allow the pharmaceutical fluid to flow from the second chamber to the first chamber to mix with the product concentrate.

In some aspects, the method further includes sealing and cutting the stem of the filtration device at a location between the filter membrane and the distal end of the syringe after introducing the pharmaceutical fluid into the syringe.

In some aspects, the method further includes performing a filter integrity test on the filter membrane after cutting the stem of the filtration device.

In some aspects, performing the filter integrity test comprises one of a pressure degradation test, a bubble point test, a water intrusion test, or a water flow test.

In some aspects, introducing the product concentrate into the bore of the syringe barrel occurs before connecting the outlet of a filtration device to the delivery opening of the syringe barrel, and before introducing the pharmaceutical fluid into the bore of the syringe barrel.

In some aspects, introducing the product concentrate into the bore of the syringe barrel occurs after connecting the outlet of a filtration device to the delivery opening of the syringe barrel, and before introducing the pharmaceutical fluid into the bore of the syringe barrel.

In some aspects, introducing the product concentrate into the bore of the syringe barrel includes either (a) introducing the product concentrate into the bore through the barrel opening at the proximal end of the syringe barrel and subsequently inserting the stopper into the barrel opening, or (b) introducing a drug product into the bore of the syringe barrel and lyophilizing the drug product while the product resides in the syringe barrel to result in the product concentrate.

Still another aspect of the present disclosure includes a method of reconstituting a medicinal or nutritional product. The method includes providing a syringe system having a first syringe comprising a syringe barrel having a proximal end defining a barrel opening, a distal end defining a delivery opening, a bore extending between the proximal end and the distal end, and a stopper disposed in the bore of the syringe barrel, a filtration device fluidly coupled to the delivery opening at the distal end of the first syringe, the filtration device comprising a stem and a filter membrane disposed in line with the stem, the filter membrane optionally having a plurality of pores each with a nominal pore size in a range of approximately 0.1 μm to approximately 0.5 μm, a second syringe comprising a syringe barrel having a proximal end defining a barrel opening, a distal end defining a delivery opening, a bore extending between the proximal end and the distal end, a stopper disposed in the bore of the syringe barrel, and a product concentrate in the bore of the second syringe barrel. The method also includes introducing a pharmaceutical fluid through the filter membrane such that a sterilized pharmaceutical fluid resides in the bore of the syringe barrel of the first syringe. The method also includes displacing the sterilized pharmaceutical fluid out of the first syringe and into the bore of the second syringe. The method also includes mixing the sterilized pharmaceutical fluid with the product concentrate in the bore of the second syringe to reconstitute the product.

In some aspects, the method also includes opening a first pathway from the filtration device to the first syringe and closing a secondpathway from the first syringe to the second syringe prior to introducing the pharmaceutical fluid through the filter membrane.

In some aspects, opening the first pathway and closing the second pathway comprises moving a first three-way valve disposed between the filtration device and the first syringe to a first configuration.

In some aspects, the method further includes opening the second pathway prior to displacing the sterilized pharmaceutical fluid out of the first syringe and to the second syringe.

In some aspects, opening the second pathway comprises moving the first three-way valve to a second configuration.

In some aspects, opening the second pathway further comprises moving a second three-way valve disposed between the first three-way valve and the second syringe to a first configuration enabling fluid communication between the second pathway and the second syringe.

In some aspects, introducing the pharmaceutical fluid through the filter membrane comprises introducing the pharmaceutical fluid through a plurality of filter membranes.

In some aspects, introducing the pharmaceutical fluid through the filter membrane comprises introducing the pharmaceutical fluid through an open outlet end and a sealed outlet end of a hollow fiber of the filter membrane.

In some aspects, introducing the pharmaceutical fluid through the filter membrane comprises introducing the pharmaceutical fluid through a filter membrane having a wall thickness in the range of approximately 150 µm to approximately 500 µm.

In some aspects, introducing the pharmaceutical fluid through the filter membrane comprises introducing the pharmaceutical fluid through a filter membrane having a longitudinal dimension in the range of approximately 3 cm to approximately 420 cm, an inner diameter in the range of approximately 2 mm to approximately 4 mm, and an outer diameter in the range of approximately 2.3 mm to approximately 5 mm.

In some aspects, introducing the pharmaceutical fluid through the filter membrane comprises introducing the pharmaceutical fluid through a filter membrane made of at least one of the following materials: a polyolefin, polyvinylidene fluoride, polymethylmethacrylate, polyacrylonitrile, polysulfone, polyethersulfone, and a polymer containing cationic charges.

In some aspects, introducing the pharmaceutical fluid through the filter membrane comprises introducing the pharmaceutical through a filter membrane having at least one U-shaped hollow fiber filter membrane secured in a U-shaped configuration by a filter membrane housing contained within a filter body.

In some aspects, introducing the pharmaceutical through a filter membrane having at least one U-shaped hollow fiber filter membrane comprises introducing pharmaceutical fluid through a plurality of U-shaped hollow fiber filter membranes.

In some aspects, introducing the pharmaceutical fluid through the filter membrane comprises introducing the pharmaceutical fluid through a plurality of parallel hollow fiber membrane filters secured in a side-by-side configuration.

In some aspects, introducing the pharmaceutical fluid through the filter membrane comprises introducing the pharmaceutical fluid through a plurality of parallel hollow fiber membrane filters arranged in a circular pattern.

In some aspects, introducing the pharmaceutical fluid through the filter membrane comprises introducing the pharmaceutical fluid through a filter membrane having a nominal pore size in a range of approximately 0.1 µm to approximately 0.22 µm.

In some aspects, the method further includes sealing and cutting the stem of the filtration device at a location between the filter membrane and the distal end of the first syringe after introducing the pharmaceutical fluid into the first syringe.

In some aspects, the method further includes performing a filter integrity test on the filter membrane after cutting the stem of the filtration device.

In some aspects, performing the filter integrity test comprises one of a pressure degradation test, a bubble point test, a water intrusion test, or a water flow test.

In some aspects, introducing the product concentrate into the bore of the second syringe comprises either (a) introducing the product concentrate into the bore through the barrel opening at the proximal end of the syringe barrel and subsequently inserting the stopper into the barrel opening, or (b) introducing a drug product into the bore of the syringe barrel and lyophilizing the drug product while the product resides in the syringe barrel to result in the product concentrate.

BRIEF DESCRIPTION OF THE DRAWINGS

While the specification concludes with claims particularly pointing out and distinctly claiming the subject matter that is regarded as the present disclosure, it is believed that the disclosure will be more fully understood from the following description taken in conjunction with the accompanying drawings. Some of the figures may have been simplified by the omission of selected elements for the purpose of more clearly showing other elements. Such omissions of elements in some figures are not necessarily indicative of the presence or absence of particular elements in any of the exemplary embodiments, except as may be explicitly delineated in the corresponding written description. None of the drawings are necessarily to scale.

FIGS. 21-24 are various perspective views showing a fifth embodiment of syringe system including a filtration device and being constructed in accordance with the principles of the present disclosure.

DETAILED DESCRIPTION

The present disclosure is directed to a novel device and method related to reconstituting a product concentrate directly in a syringe barrel. Generally, the syringe barrel includes at least one chamber and is provided to a hospital or pharmacist, for example, with a product concentrate pre-filled therein. On demand, a pharmacist can introduce a pharmaceutical fluid such as a diluent into the empty chamber through a sterilization filter such that the sterilized pharmaceutical fluid can be used to reconstitute the product concentrate into a sterile, patient deliverable product. Subsequent to reconstitution, but prior to patient administration, the sterilizing filter can be removed from the syringe and tested to ensure proper filtration was achieved.

To meet the foregoing, the present disclosure provides various embodiments of syringe systems. A first embodiment described primarily with reference to FIG. 1 includes a conventional single chamber syringe with a sterilizing filter attached to its administration end for receiving a pharmaceutical fluid during the reconstitution process. A second embodiment described primarily with reference to FIG. 2 includes a system similar to FIG. 1 but the syringe is a dual chamber syringe with a sterilizing filter attached to its administration end for receiving a pharmaceutical fluid during the reconstitution process. The dual-chamber syringe may allow for the provision of product concentrate in one chamber and diluent in the other, while maintaining separation between the two until mixing is desired. This may allow some flexibility in the process of introducing diluent on-demand. A third embodiment described primarily with reference to FIG. 3 includes a system similar to FIGS. 1 and 2 but the sterilization filter is connected to the syringe via a valving mechanism and includes an additional administration port separate the filtration device. This arrangement may allow some flexibility in the types of administration connections that can be achieved. Fourth and fifth embodiments are described with reference to FIG. 4 and FIGS. 21-24, respectively, each including a system with two separate syringes in selective communication with one another via a valving arrangement. A first syringe is empty and initially fluidly coupled to a sterilization filter, while the second syringe can be pre-filled with a product concentrate. Similar to the dual-chamber system, this dual-syringe system may allow for the provision of product concentrate in one syringe and diluent in the other, while maintaining separation between the two until mixing is desired. This may allow some flexibility in the process of introducing diluent on-demand. Each of these embodiments will now be described in more detail.

Figure 1:
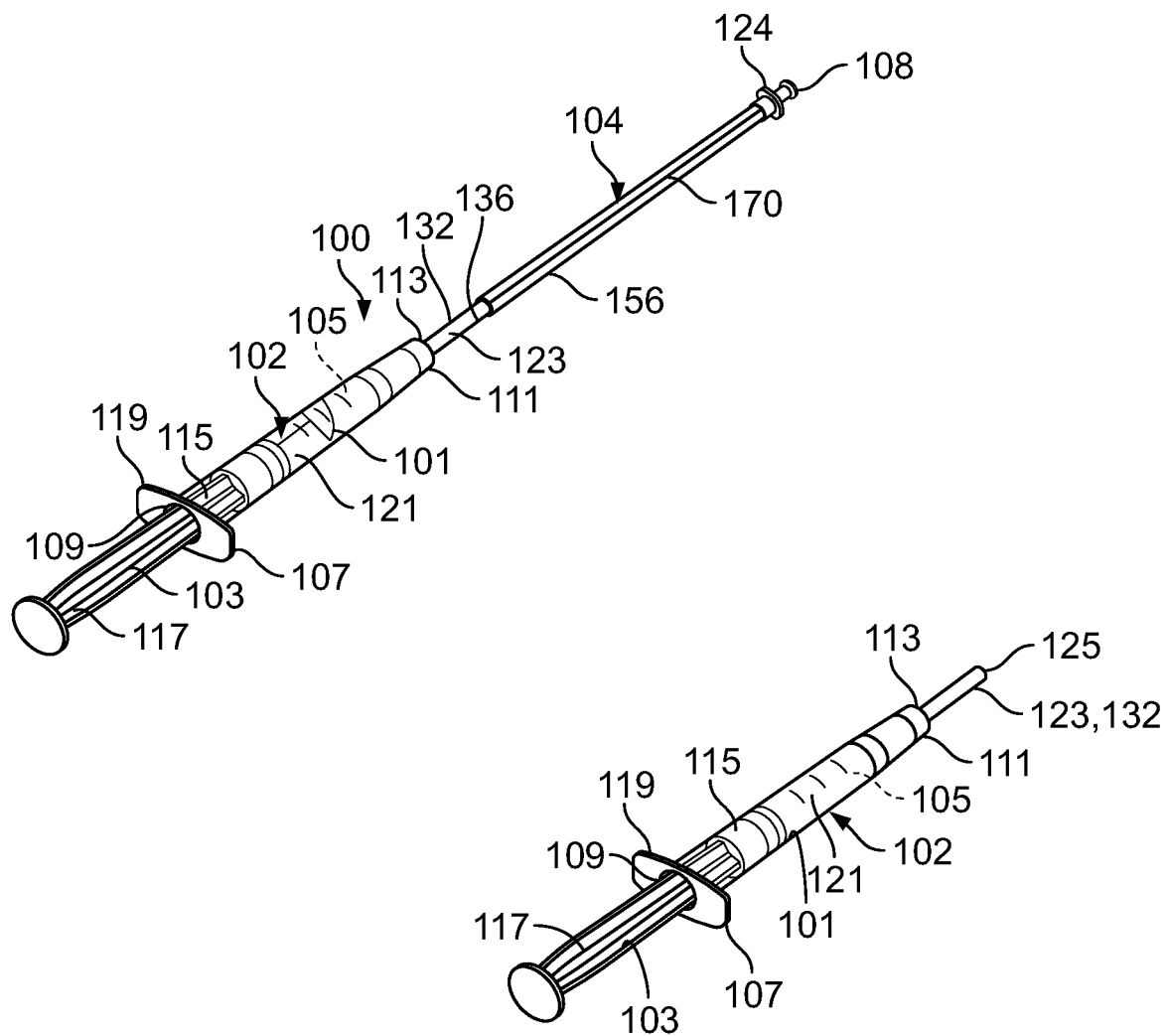
FIG. 1 illustrates perspective views of a first embodiment of a syringe system including a filtration device and a syringe with the filtration device removed, both being constructed in accordance with the principles of the present disclosure.

FIG. 1 illustrates a first embodiment of a syringe system 100 constructed in accordance with the principles of the present disclosure including a syringe 102 and a filtration device 104 attached to the syringe 102. FIG. 1 illustrates the syringe 102 coupled to the filtration device 104 and the syringe 102 with the filtration device 104 removed. The syringe 102 can include a relatively conventional syringe in that it includes a syringe barrel 101 and a plunger assembly 103 slidably disposed in the syringe barrel 101. More specifically, the syringe barrel 101 includes a proximal end 107 carrying a finger flange 119 and defining a barrel opening 109, a distal end 111 defining a delivery opening 113 and carrying a connection fitting (not shown) such as a Luer connector, and a hollow bore 105 extending between the proximal and distal ends 107, 109. The plunger assembly 103 includes a stopper 115 and a plunger rod 117, the stopper 115 being slidably disposed in the bore 105. So configured, when the bore 105 of the barrel 101 contains a fluid such as a medicament or nutrient solution for patient administration, a user can depress the plunger rod 117 in a known manner to express the fluid out of the delivery opening 113 at the distal end 111 of the barrel 101.

In some embodiments, the syringe 102 of FIG. 1 can be pre-filled with a product concentrate 121 that requires reconstitution prior to patient administration. In some versions, the concentrate 121 can be introduced into the bore 105 either before or after the syringe 102 is attached to the filtration device 104. That is, in some versions, either before or after the filtration device 104 is attached to the syringe 102, the product concentrate 121 can be introduced into the bore 105 through the barrel opening 109 and then the plunger assembly 103 can be inserted into the bore 105 to seal the barrel opening 109. In other versions, the product solution can be introduced into the bore 105 of the barrel 101 and subsequently lyophilized in the barrel 101. This lyophilization could occur in the absence of the plunger assembly 103 such that water vapor exhausts out of the barrel opening 109, or with the plunger assembly 103 sealing the barrel opening 109, in which case water vapor can exhaust through the filtration device 104.

The filtration device 104, as mentioned, is attached to the distal end 111 of the syringe barrel 101 and, in the version depicted in FIG. 1, includes a stem 156, a filter membrane 170 disposed in-line with the stem 156, and a sterile closure cap 108. In the depicted version, the filter membrane 170 can include a hollow tubular filter membrane disposed inside of the stem 156, examples of which will be described below. In other versions, however, other filter membrane arrangements can be used. The stem 156 is a hollow narrow tube having an inlet 124 and an outlet 136 fluidly connected to the delivery opening 113 of the syringe barrel 101. The sterile closure cap 108 sealably covers the inlet 124 of the stem 156 to maintain sterility until necessary to remove the cap 108 during use. In other versions, the system does not include a cap 108, but rather, can include a split septum or membrane disposed in the stem 156 adjacent the inlet 124, and which can be pierced by a filling tube or nozzle being inserted into the inlet 124.

So configured, a pharmaceutical fluid such as a water, saline, a solution, a diluent, etc., may be introduced into the inlet 124 of the stem 156, and passed through the filter membrane 170, out of the outlet 136, which leads to the delivery opening 113 and bore 105 of the syringe barrel 101.

In those embodiments where the bore 105 of the syringe 102 is pre-filled with a product concentrate 121, the introduction of the pharmaceutical fluid through the filtration device 104 can be followed by a mixing of the pharmaceutical fluid with the concentrate 121 to reconstitute to the concentrate 121 into a patient deliverable product. Mixing may occur without manual manipulation of the syringe 102, or may be influenced by tipping, shaking, or otherwise imparting forces onto the syringe 102 to ensure mixing.

With continued reference to FIG. 1, a portion of the stem 156 disposed between the outlet 136 and the distal end 111 of the syringe barrel 101 can include a port tube 123. This port tube 123 can be identified as a "seal and cut area." The phrase "seal and cut area" 132 pertains to the manner in which the syringe bore 105 is sealed and the filtration device 104 cut off after introducing fluid to the syringe 101 through the filtration device 104. That is, the disclosed arrangement is designed such that after the bore 105 receives fluid from the filtration device 104, a sealing mechanism can be employed to seal the stem 156 closed in the "seal and cut area," which is between the filter membrane 170 and the distal end 111 of the syringe 102. Thus, the "seal and cut area" 132 in this version is a portion of the stem 156 where the filter membrane 170 does not reside. Sealing of the "seal and cut area" 132 can be achieved with a heat sealer or any other device, including for example clamping a clamp onto the "seal and cut area" 132. Once the stem 156 is sealed, the stem 156 is cut at a location above the seal but below the filter membrane 170 to seal off the bore 105 of the syringe 102. Cutting may be achieved with a knife or any other device.

To ensure that the filter membrane 170 performed properly, a filter integrity test can be performed on the filter membrane 170. A filter integrity test is facilitated by the arrangement of the "seal and cut area" (second part 132) of the stem 156, which allows for the filtration device 104 and, more specifically, the filter membrane 170 of the filtration device 104 to be separated intact from the remainder of the now-sealed syringe 105. For example, after the stem 156 and filter membrane 170 are separated from the syringe 105, a filter testing device (not shown) may be pre-programmed or controlled to perform a filter integrity test on the filter membrane 170. Examples of filter integrity tests might include a bubble point test, a pressure degradation test, a water intrusion test, a water flow test, or any suitable test known in the art. A pressure degradation test is a method for testing the quality of a filter either before or after the filter has been used. In the preferred embodiment, the filter membrane 170 is tested after the solution passes through the filter membrane 170 and into the bore 105 of the syringe 102. To perform the filter integrity test using a pressure degradation test procedure, a test head (not shown) engages the stem 156 and applies an air pressure of a predetermined value to the inlet 124 and filter membrane 170. In one embodiment, the pre-determined value is the pressure where gas cannot permeate the filter membrane 170 of an acceptable filter membrane 170. A pressure sensor, or other method of measuring the integrity of the filter membrane 170, is located within the test head and measures the pressure decay or diffusion rate through the filter membrane 170. The results from the integrity test are assessed to determine the quality of the filter membrane 170, and therefore the quality of the solution that previously passed through the filter membrane 170 and into the syringe 102. If the pressure sensor measures a decay or a unexpected rate of decay, then the filter membrane 170 fails the test and it can be determined that the solution in the syringe 105 is unsatisfactory.

Alternatively in a bubble point test, the test head gradually increases the pressure applied to the filter membrane 170, and the increase in pressure is measured in parallel with the diffusion rate of the gas through the filter membrane 170. Any disproportionate increase in diffusion rate in relation to the applied pressure may indicate a hole or other structural flaw in the filter membrane 170, and the filter membrane 170 would fail the integrity test.

Thus, it can be appreciated that the disclosed arrangement of the "seal and cut area" 132 of the syringe system 100 of FIG. 1 advantageously facilitates the filter integrity test, and a determination that the fluid in the syringe 102 is either sterile or has the potential of being compromised may be made with a high degree of certainty.

As mentioned above, the stem 156 provides an isolated fluid connection between the inlet 124 of the filtration device 104 and the bore 105 of the syringe 102, such that once the fluid is filtered through the filter membrane 170, the filtered fluid passes directly into the sterilized environment of the bore 105 of the syringe 102. Hence, after the bore 105 of the syringe 102 receives the sterilized fluid and the stem 156 is sealed and cut, this results in a sealed syringe 102, as illustrated on the right-hand side of FIG. 1. Specifically, a tip 125 of the port tube 123 is heat sealed closed such that the fluid in the bore 105 of the syringe 102 remains sterile until the syringe 102 is opened, punctured, or otherwise compromised. This sealed tip 125 of the port tube 123 serves as a tip protector for the syringe 102, particularly protecting the distal end 111, until it is removed from the syringe 102 by a nurse or other technician to connect to a needle or Luer Activated Device (LAD), for example. That is, to subsequently administer the contents of the syringe 102 to a patient, the port tube 123 can be removed from the distal end 111 of the syringe 102 and the syringe 102 can be attached to a conventional delivery needle with a standard connection or perhaps directly to a LAD as is known in the art.

Figure 2:
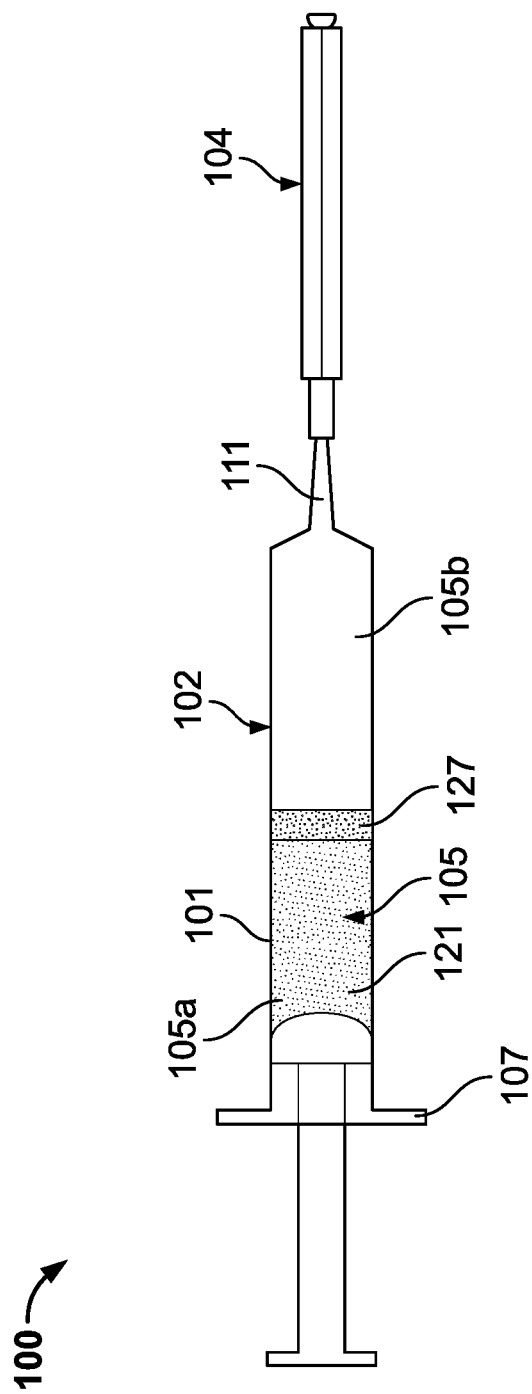
FIG. 2 illustrates a side view of a second embodiment of a syringe system including a filtration device and being constructed in accordance with the principles of the present disclosure.

As mentioned above, the syringe 102 of the syringe system 100 of the present disclosure may be pre-filled with a product concentrate 121 that requires reconstitution prior to patient administration. The syringe 102 of FIG. 1 can be used to contain product concentrate 121 directly in the bore 105 of the barrel 101. FIG. 2 depicts an alternative embodiment of the system 100, however, where the syringe 102 includes a dual chamber syringe. Specifically, the system 100 includes a syringe 102 and a filtration device 104 attached to the syringe 102. The system of FIG. 2 is substantially similar to that of FIG. 1 so only the differences will be described in any detail. Specifically, the syringe 102 includes a syringe barrel 101 including a bore 105 divided into a first chamber 105a and a second chamber 105b separated by a dual-chamber stopper 127. The first chamber 105a is disposed between the dual-chamber stopper 127 and the proximal end 107 of the syringe barrel 101. The second chamber 105b is disposed between the dual-chamber stopper 127 and the distal end 111 of the syringe barrel 101. That is, the dual-chamber stopper 127 provides a fluid tight seal with the syringe barrel 101 to prevent all fluid communication between the first and second chambers 105a, 105b, until desired. So configured, the first chamber 105a can be pre-filled with a product concentrate 121 stored in a sterile environment. When it is desired to reconstitute the concentrate 121 and deliver the reconstituted product to a patient, a pharmaceutical fluid can be introduced into the second chamber 105b through the filtration device 104 in a manner same as that described above with reference to FIG. 1. The stem 156 of the filtration device 104 can be sealed and cut, the integrity of the filtration device 104 can be tested. Then, the dual-chamber stopper 127 can be moved to open a flow path between the first and second chambers 105a, 105b, which allows the pharmaceutical fluid in the second chamber 105b to mix with the concentrate 121 in the first chamber 105a to reconstitute the final product. Subsequent steps for patient administration can be identical to those suggested above with respect to the system 100 of FIG. 1.

Figure 3:
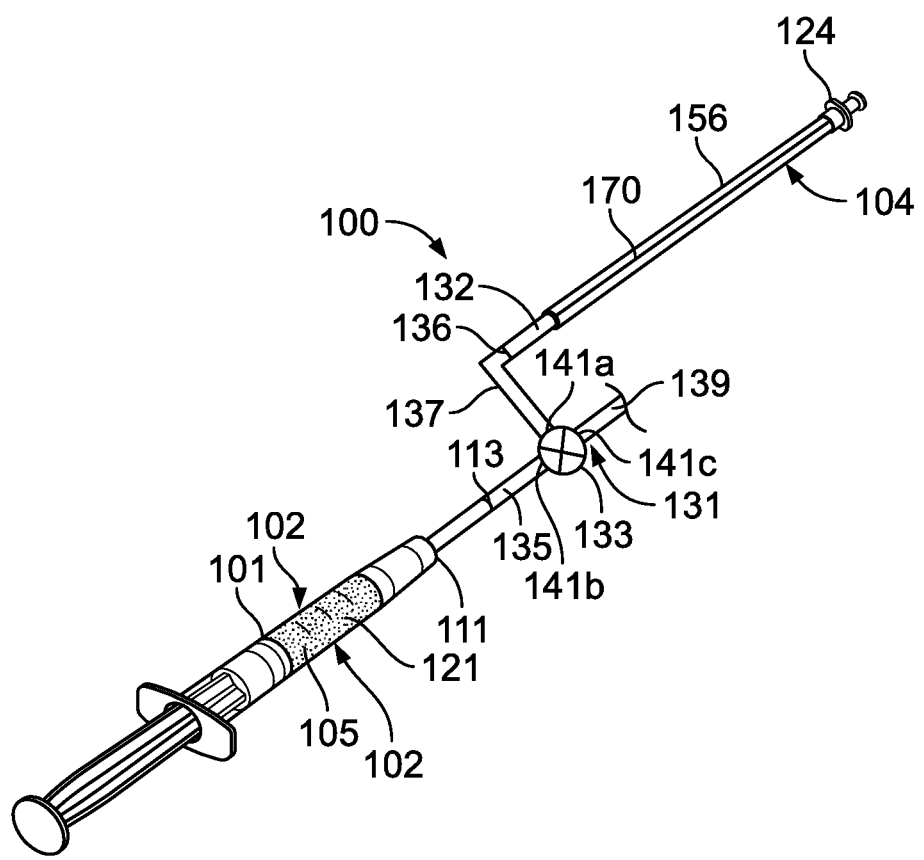
FIG. 3 illustrates a perspective view of a third embodiment of syringe system including a filtration device and being constructed in accordance with the principles of the present disclosure.

While the systems 100 in FIGS. 1 and 2 have included the seal and cut area 132 of the stem 156 immediately adjacent to the distal end 111 of the syringe 102 for sealing the syringe 102 and removing the filtration device 104 for integrity testing, other embodiments can be configured differently. For example, FIG. 3 depicts an alternative embodiment of a syringe system 100 constructed in accordance with the principles of the present disclosure including a syringe 102, a filtration device 104 attached to the syringe 102, and a valving arrangement 131 disposed between the filtration device 104 and the syringe 102. The valving arrangement includes a three-way valve 133, a port tube 135, a fill tube 137, and an administration tube 139. The three-way valve 133 includes a first port 141a, a second port 141b, and a third port 141c. The fill tube 137 is connected between the first port 141a of the three-way valve 133 and the outlet 136 of the filtration device 104. The port tube 135 is connected between the second port 141b of the three-way valve 133 and the delivery opening 113 at the distal end 111 of the syringe 102. The administration tube 139 is connected to the third port 141c of the three-way valve 133 and is adapted to be connected to an administration set, for example, during patient administration.

With the configuration illustrated in FIG. 3, the bore 105 of the syringe 102 can again be provided empty or pre-filled with a product concentrate 121 as described above. Moreover, the bore 105 of the syringe 102 may include a single chamber as described with reference to FIG. 1 or can be a dual-chamber syringe as described with reference to FIG. 1. Furthermore, the filtration device 104 can be identical to the filtration devices described above. Accordingly, the detail and operation of these components need not be repeated.

When the syringe 102 is pre-filled with a product concentrate 121 and a pharmacist or other handler is prepared to reconstitute the product for patient delivery, a pharmaceutical fluid can be introduced into the syringe barrel 101 via the filtration device 104. First, the three-way valve 133 is manipulated to a first configuration which opens fluid communication between the first and second ports 141a, 141b, but closes fluid communication between the second and third ports 141b, 141c. This can be achieved by a manual manipulation of a knob or lever provided on the three-way valve 133, for example. In this first configuration of the three-way valve 133, the filtration device 104 is freely open to communicate with the syringe 102. Accordingly, a pharmaceutical fluid can be introduced into the inlet 124 of the stem 156 of the filtration device 104. This fluid is then sterilized by passing through the filter membrane 170. The sterilized fluid then travels out of the outlet 136 of the stem 156 and into the fill tube 137, through the first port 141a and out of the second port 141b of the three-way valve 133. Finally, the sterilized fluid passes through the port tube 135 and into the bore 105 of the syringe 102 via the delivery opening 113.

With a desired amount of sterilized pharmaceutical fluid introduced into the syringe 102 via the filtration device 104, the stem 156 can be sealed and cut at the "seal and cut" area 132 located adjacent to the outlet 136 of the stem 156. In some versions, because the system 100 includes the three-way valve 133, the stem 156 may not necessarily need to be sealed before cutting. Sealing the stem 156 therefore seals access to the syringe 102, and cutting allows for the filtration device 104 to undergo integrity testing as described above. With the stem 156 sealed, the pharmaceutical fluid in the syringe 102 can be mixed with the product concentrate 121 to reach a desired product mixture for patient administration. When ready for administration, the administration tube 139 can be connected to an administration set such as a LAD or needle. Then, the three-way valve 133 can be manipulated to a second configuration where the second port 141b is fluidly connected to the third port 141c, but not fluidly connected to the first port 141a. Thus, the syringe 102 is in fluid communication with the administration tube 139 for patient delivery. While the foregoing version of the system in FIG. 3 has been described as including the step of sealing the stem 156 prior to cutting, in alternative versions, the three-way valve 133 could be equipped with a third configuration wherein each of the first, second, and third ports 141a, 141b, 141c is closed off from the other ports 141a, 141b, 141c. Thus, when the three-way valve 133 occupies this third configuration, the sterility of the product concentrate and pharmaceutical fluid in the bore 105 of the syringe 102 would be maintained.

Figure 4:
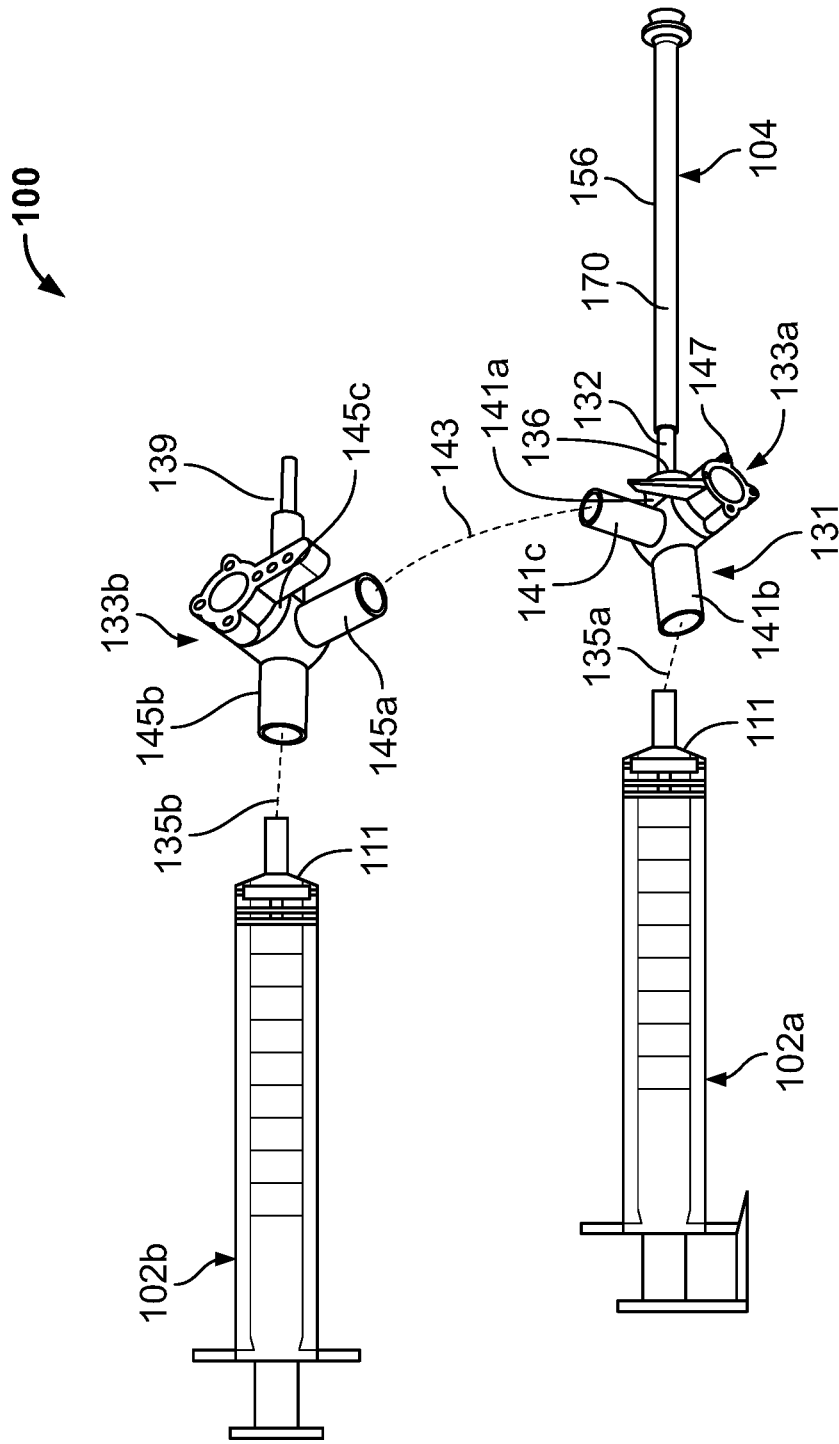
FIG. 4 illustrates a perspective view of a fourth embodiment of syringe system including a filtration device and being constructed in accordance with the principles of the present disclosure.

While each of the foregoing embodiments of the syringe system 100 of the present disclosure have included a single syringe 102, other embodiments can be arranged otherwise. For example, FIG. 4 depicts one alternative embodiment of a syringe system 100 constructed in accordance with the principles of the present disclosure and including a first syringe 102a, a filtration device 104, a second syringe 102b, and a valving arrangement 131 providing selective fluid flow communication between the filtration device 104 and the first syringe 102a, and between the first syringe 102a and the second syringe 102b. The construct of the filtration device 104 and each of the first and second syringes 102a, 102b can be identical to the same components described above such that the details will not be repeated.

The valving arrangement 131 includes a first three-way valve 133a, a first port tube 135a, a diverter tube 143, a second three-way valve 133b, a second port tube 135b, and an administration tube 139. In FIG. 4, the first and second port tubes 135a, 135b and the diverter tube 143 are illustrated schematically with broken lines, but it should be appreciated that these would include conventional tubular fluid lines or something equivalent.

The first three-way valve 133a is disposed between the filtration device 104 and the first syringe 102a for selectively controlling fluid communication between the filtration device 104 and the first syringe 102a, and also between the first syringe 102a and the second syringe 102b. More specifically, the first three-way valve 133a includes a first port 141a, a second port 141b, and a third port 141c. The first port 141a is connected to the outlet 136 of the stem 156 of the filtration device 104. The second port 141b is connected to the delivery opening 113 at the distal end 111 of the first syringe 102a via the first port tube 135a. The third port 141c is connected to the diverter tube 143.

The second three-way valve 133b is disposed between the second syringe 102b and the administration tube 139 for selectively controlling fluid communication between the first syringe 102a and the second syringe 102b, and between the second syringe 102b and the administration tube 139. More specifically, the second three-way valve 133b includes a first port 145a, a second port 145b, and a third port 145c. The first port 145a is connected to the diverter tube 143. The second port 145b is connected to the delivery opening 113 at the distal end 111 of the second syringe 102a via the second port tube 135b. The third port 145c is connected to the administration tube 139.

With the configuration illustrated in FIG. 4, the second syringe 102b is configured to contain a product concentrate (not shown in FIG. 4), while the first syringe 102a is adapted to receive a sterilized pharmaceutical fluid via the filtration device 104 and subsequently mix that pharmaceutical fluid into the second syringe 102b to reconstitute the product concentrate 121.

Accordingly, when a pharmacist or other handler is prepared to reconstitute the product for patient delivery, a pharmaceutical fluid can be introduced into the first syringe 102a via the filtration device 104. First, the first three-way valve 133a is manipulated into a first configuration which opens fluid communication between the first and second ports 141a, 141b, but closes fluid communication between the second and third ports 141b, 141c. This can be achieved by a manual manipulation of a knob or lever 147 provided on the first three-way valve 133a, for example. In this first configuration of the first three-way valve 133a, the filtration device 104 is freely open to communicate with the first syringe 102a. Accordingly, a pharmaceutical fluid can be introduced into the inlet 124 of the stem 156 of the filtration device 104. This fluid is then sterilized by passing through the filter membrane 170. The sterilized fluid then travels out of the outlet 136 of the stem 156, through the first port 141a and out of the second port 141b of the first three-way valve 133a. Finally, the sterilized fluid passes through the first port tube 135a and into the bore 105 of the first syringe 102a.

With a desired amount of sterilized pharmaceutical fluid introduced into the first syringe 102a via the filtration device 104, the stem 156 can be sealed and cut at the "seal and cut" area 132 located adjacent to the outlet 136 of the stem 156. Sealing the stem 156 therefore seals access to the first syringe 102a, and cutting allows for the filtration device 104 to undergo integrity testing as described above.

Next, it is necessary to move the sterilized pharmaceutical fluid from the first syringe 102a to the second syringe 102b to reconstitute the product concentrate container therein. To achieve this, the first three-way valve 133a can be manipulated to a second configuration where the second port 141b is fluidly connected to the third port 141c, but not fluidly connected to the first port 141a. Additionally, the second three-way valve 133b can be manipulated into a first configuration where its first port 145a is in fluid communication with its second port 145b, but not with the third port 145c. Thus, with the first three-way valve 133a in its second configuration and the second three-way valve 133b in its first configuration, the first syringe 102a is in fluid communication with the diverter tube 143, which is in fluid communication with the second syringe 102b. So configured, a user can force the sterilized pharmaceutical fluid from the first syringe 102a using the plunger assembly 103 in a known manner, through the first three-way valve 133a, through the diverter tube 143, through the second three-way valve 133b, and into the second syringe 102b to mix with the product concentrate. To the extent necessary, a user may further desire to force the mixture back and forth between the first and second syringes 102a, 102b to ensure complete and thorough reconstitution of the product.

Once the product is sufficiently reconstituted it can be stored in the second syringe 102b and the second three-way valve 133b can be manipulated into a second configuration where the second port 145b is in fluid communication with the third port 145c, but not the first port 145a. So configured, the second syringe 102b is in fluid communication with the administration tube 139, which again can be connected to an administration set, a LAD, or a needle for example, for patient administration. Manual depression of the plunger assembly 103 on the second syringe 102b can thus force the mixed product out of the second syringe 102b to the patient.

As with the embodiment in FIG. 3, the first three-way valve 133a of the system of FIG. 4 could be equipped with a third configuration wherein each of the first, second, and third ports 141a, 141b, 141c is closed off from the other ports 141a, 141b, 141c. Thus, when the first three-way valve 133a occupies this third configuration, the sterility of the product concentrate and pharmaceutical fluid in the bore 105 of the first syringe 102a would be maintained. This could be an alternative to sealing the stem 156 prior to cutting the filtration device 104 off of the system 100 for testing.

FIGS. 21-24 depict another embodiment of a syringe system 1100 constructed in accordance with the principles of the present disclosure and including a first syringe 1102a, a filtration device 1104, a second syringe 1102b, and a valving arrangement 1131 providing selective fluid flow communication between the filtration device 1104 and the first syringe 1102a, and between the first syringe 1102a and the second syringe 1102b. The construct of the first and second syringes 1102a, 1102b can be identical to any of the same components described above such that the details will not be repeated.

The valving arrangement 1131 includes a three-way valve 1133 with a single body defining a first port 1135a, a second port 1135b, and a third port 1135c. Internally, the three-way valve 1133 can define a Y-shaped passageway 1139 including a first path 1139a, a second path 1139b, and a third path 1139c. The first port 1135a is coupled to and in fluid communication with the filtration device 1104, the second port 135b is coupled to and in fluid communication with the first syringe 1102a, and the third port is coupled to and in fluid communication with the second syringe 1102b. As also depicted, the three-way valve 1133 includes a switch 1137 operably coupled to a valve member (not shown) disposed inside of the body of the three-way valve 1133. The switch 1137 can be manually manipulated between a first position depicted in FIG. 21, wherein the three-way valve 1133 occupies a first configuration, and a second position depicted in FIGS. 22A-22C, wherein the three-way valve 1133 occupies a second configuration. In the first position of the switch and 1137 and first configuration of the valve 133, the first syringe 1102a is in fluid communication with the filtration device 1104 via the first and second paths 1135a, 1135b, and not in fluid communication with the second syringe 1102b. In the second position of the switch 1137 and the second configuration of the valve 1133, the first syringe 1102a is in fluid communication with the second syringe 1102b via the second and third paths 1135b, 1135c, and not in communication with the filtration device 1104.

Figure 21:
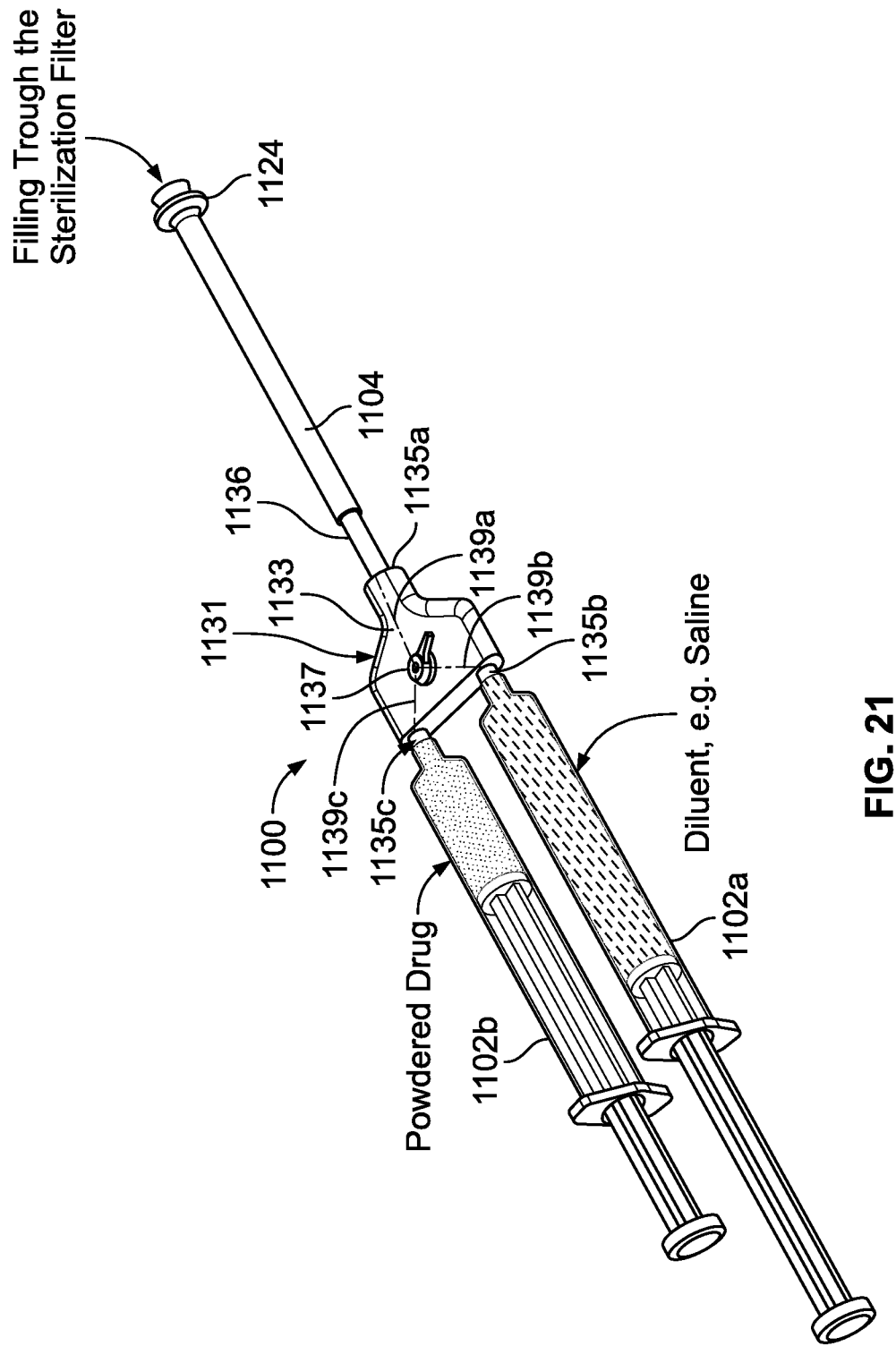

With the configuration illustrated in FIG. 21, the second syringe 1102b is initially configured to contain a product concentrate (not shown), while the first syringe 1102a is adapted to receive a sterilized pharmaceutical fluid via the filtration device 1104 and subsequently mix that pharmaceutical fluid into the second syringe 1102b to reconstitute the product concentrate in a manner similar to that described above in reference to FIG. 4, for example.

Accordingly, when a pharmacist or other handler is prepared to reconstitute the product for patient delivery, a pharmaceutical fluid can be introduced into the first syringe 1102a via the filtration device 1104. First, the first three-way valve 1133 is manipulated into the first position (FIG. 21) which opens fluid communication between the first syringe 1102a and the filtration device 1104. This can be achieved by a manual manipulation of the switch, as mentioned above. Accordingly, a pharmaceutical fluid can be introduced into an inlet 1124 of the filtration device 1104. This fluid is then sterilized by passing through a filter membrane of the filtration device 1104. The sterilized fluid then travels out of an outlet 1136 of the filtyration device 1104, through the first port 1135a and out of the second port 1135b of the three-way valve 1133. Finally, the sterilized fluid passes directly into the first syringe 1102a. As the first syringe 1102a is filled, a user may slowly withdraw the plunger from the syringe 1102a to accommodate receipt of the fluid.

Figure 22A:
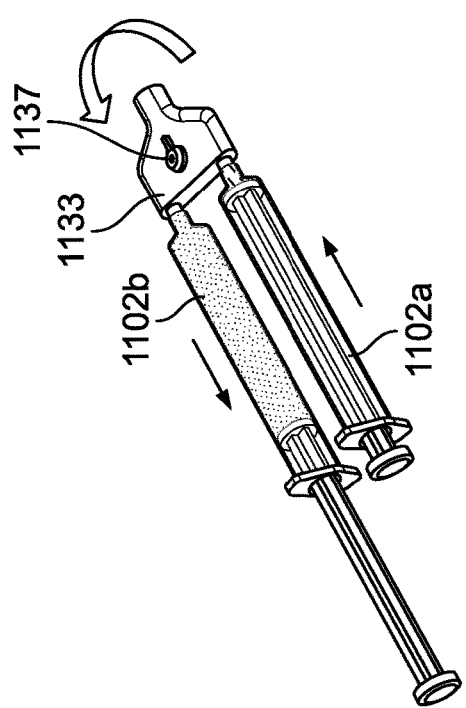
Figure 22B:
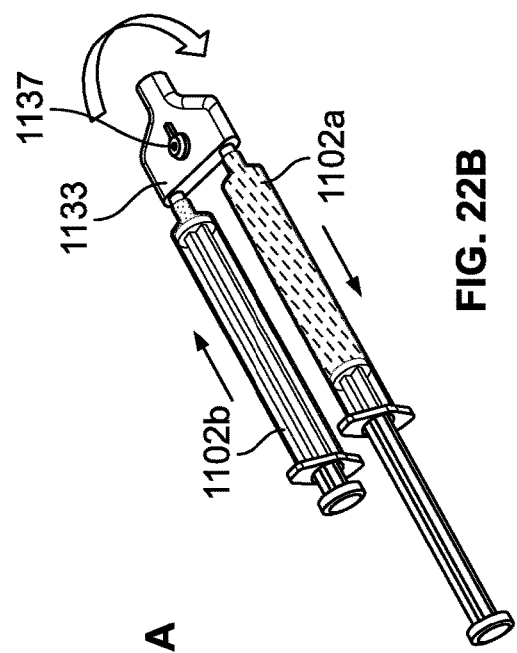
Figure 22C:
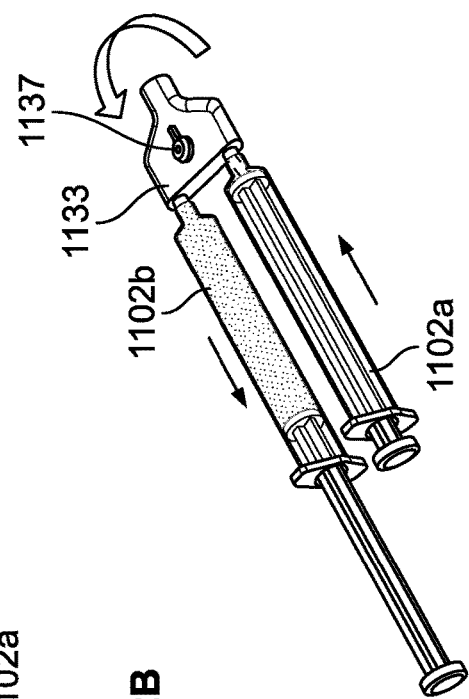

With a desired amount of sterilized pharmaceutical fluid introduced into the first syringe 1102a, the filtration device 1104 can be sealed and cut in a manner identical to that described above with other embodiments, and finally integrity tested to ensure the sterility of the fluid in the first syringe 1102a. The device with the filtration device 1104 removed is illustrated in FIGS. 22A-22C.

Next, it is necessary to move the sterilized pharmaceutical fluid from the first syringe 1102a to the second syringe 1102b to reconstitute the product concentrate contained therein. To achieve this, the switch 1137 on the three-way valve 1133 can be manipulated to the second position, which is shown in FIGS. 22A-22C. Here, the first syringe 1102a is in fluid communication with the second syringe 1102b via the third port 1135c, but not with the first port 1135a. In fact in some versions, the first port 1135a is sealed off because in order to remove the filtration device 1104 for integrity testing, the filtration device 1104 is sealed and cut a at a location adjacent to the first port 1135a. As such, in some versions, with the switch 1137 in the second position, the first syringe 1102a may continue to be in fluid communication with the first port 1135a, but the first port 1135a is sealed closed so no fluid can pass therethrough. Instead, all fluid leaving the first syringe 1102a will flow to the second syringe 1102b.

So configured, a user can force the sterilized pharmaceutical fluid from the first syringe 1102a using the plunger in a known manner, through the three-way valve 1133, and into the second syringe 1102b to mix with the product concentrate. This can be seen with the arrows presented on FIG. 22A, where the plunger on the first syringe 1102a is depressed and the plunger on the second syringe 1102b is withdrawn. To the extent necessary, a user may further desire to force the mixture back and forth between the first and second syringes 1102a, 1102b, as illustrated in FIGS. 22b and 22C, to ensure complete and thorough reconstitution of the product. During this mixing between the first and second syringes 1102a, 1102b, the switch 1137 remains in the second position.

Once the product is sufficiently reconstituted it can be stored in the second syringe 1102b, as illustrated in FIG. 23. Then, for patient administration, the second syringe 1102b can be removed from the three-way valve 1133 and a delivery needle 1141 can be attached, as illustrated in FIG. 24.

As mentioned, the filtration device 104 of the various systems 100 of the present disclosure are capable of sterilizing fluid as it passes through the filter membrane 170. The filtration device 104 and filter membrane 170 can take various forms and the present disclosure is not necessarily limited to any one form.

Figure 5:
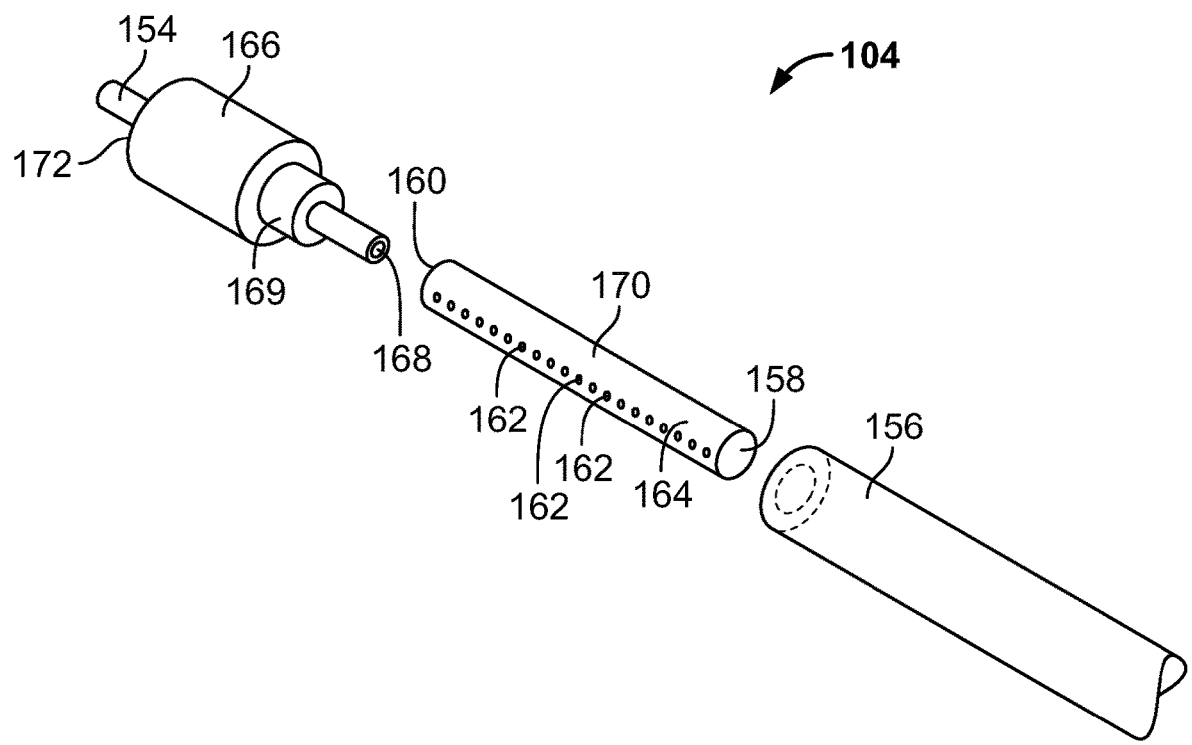
FIG. 5 is an expanded isometric view of one embodiment of a filtration device for use with the syringe system of the present disclosure.
Figure 6:
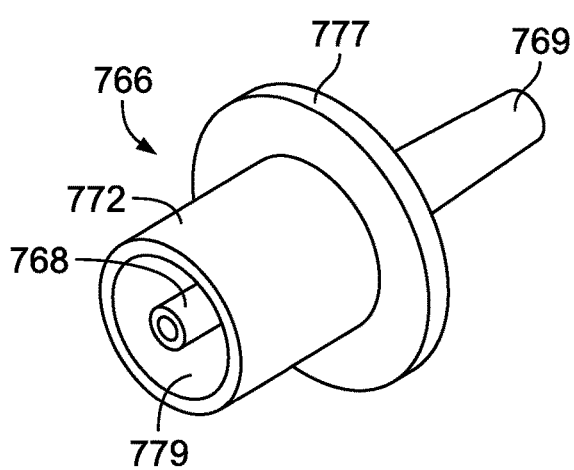
FIG. 6 is a perspective view of an alternative connector for use with the filtration device for use with the syringe system of the present disclosure.
Figure 7:
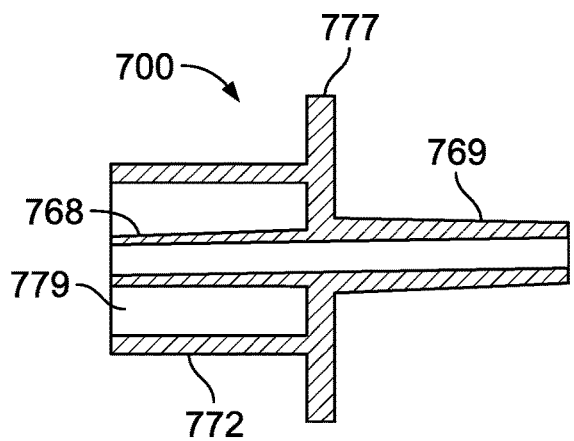
FIG. 7 is a side cross-sectional view of the connector of FIG. 6.
Figure 8:
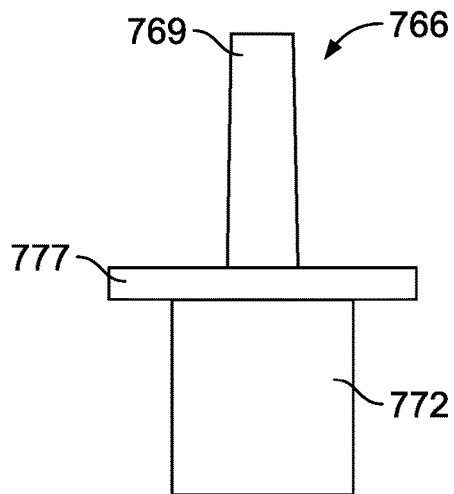
FIG. 8 is a side view of the connector of FIG. 6.
Figure 9:
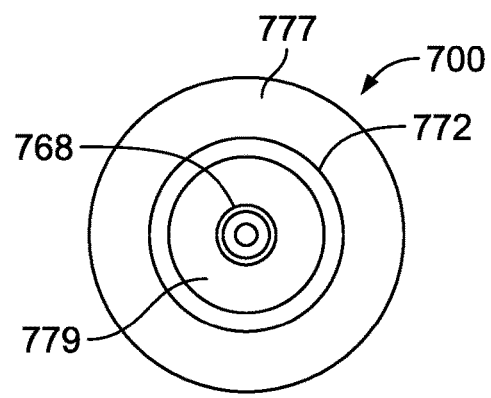
FIG. 9 is a bottom view of the connector of FIG. 8.
Figure 10:
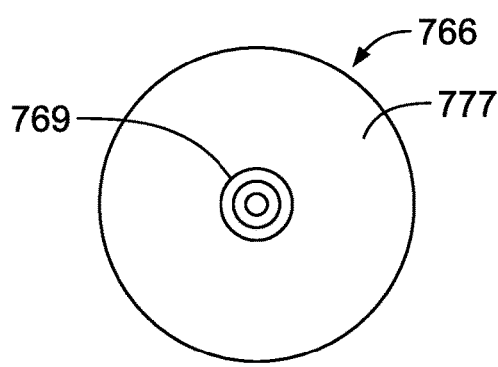
FIG. 10 is a top view of the connector of FIG. 8.

For example, FIG. 5 illustrates one embodiment of a filtration device 104 for use with any of the syringe systems 100 describe above in FIGS. 1-4 and 21-24. The filtration device 104 can include a hollow fiber membrane 170 with one sealed end 158 and one open inlet end 160. The sealed end 158 can be capped or it may be sealed with a heat seal, an adhesive, or some other means. A plurality of pores 162 along the surface 164 of the filter membrane 170 allow a pharmaceutical fluid that entered the filter membrane 170 at the open inlet end 160 to exit the filter membrane 170. In one version, the stem 156 surrounds the filter membrane 170 in a generally concentric configuration so filtered pharmaceutical fluid exiting the filter membrane 170 is contained within the stem 156 and ultimately passed out of the outlet 136 of the filtration device 104.

As depicted in FIG. 5, a hollow connector 166 can be used to secure the stem 156 and the filter membrane 170 together. The open inlet end 160 of the filter membrane 170 is sealingly connected to an open outlet end 168 of the hollow connector 166. The connection may be achieved by gluing the open inlet end 160 of the filter membrane 170 to the open outlet end 168 of the connector 166 with, for example, an epoxy resin, a polyurethane resin, a cyanoacrylate resin, a UV curing acrylic adhesive, or a solvent for the material of the hollow connector 166 such as cyclohexanone. In the version depicted, the open outlet end 168 of the connector 166 comprises a hollow cylindrical member that fits inside of and is fixed to the open inlet end 160 of the filter membrane 170. As such, an outer diameter of the open outlet end 168 of the connector 166 is substantially similar to or slightly smaller than an inner diameter of the open inlet end 160 of the filter membrane 170. In some versions, the open inlet end 160 of the filter membrane 170 may be welded to the open outlet end 168 of the connector 166 by, for example, heat welding (e.g., introducing a hot conical metal tip into the open inlet end 160 of the filter membrane 170 to partially melt it), laser welding if the hollow connector 166 is made from a material that absorbs laser radiation, mirror welding, ultrasound welding, and friction welding. Alternately, the filter membrane 170 may be inserted into a mold, and a thermoplastic polymer may be injection-molded around it to form the hollow connector 166. Other designs and configurations for connecting the filter membrane 170 to the connector 166 are intended to be within the scope of the present disclosure.

The hollow connector 166 further includes a fluid inlet 169. A pharmaceutical fluid can be fed via a connected fluid supply line, for example, into the fluid inlet 169 of the hollow connector 166. In some versions, the fluid inlet 169 can include a Luer type fitting or other standard medical fitting. The pharmaceutical fluid can then travel through the hollow connector 166 and exit into the filter membrane 170 through the open outlet end 168 of the hollow connector 166. The hollow connector 166 also includes a sealing surface 172 to which the stem 156 is attached. The sealing surface 172 in this version is cylindrical and has a diameter larger than a diameter of the open outlet end 168, and is disposed generally concentric with the open outlet end 168. In fact, in this version, the outer diameter of the sealing surface 172 is generally identical to or slightly smaller than an inner diameter of the stem 156. So configured, the stem 156 receives the sealing surface 172 and extends therefrom to surround and protect the filter membrane 170 without contacting the surface 164 of the filter membrane 170. The stem 156 can be fixed to the sealing surface 172 with adhesive (e.g., a UV curing acrylic adhesive), epoxy, welding, bonding, etc. The stem 156 receives the pharmaceutical solution after it passes through the pores 162 in the filter membrane 170. From there, the now filtered solution passes out of the outlet 136 of the stem 156.

FIGS. 6-10 illustrate an alternative hollow connector 766, similar to connector 166, for securing the stem 156 and the hollow fiber filter membrane 170 of FIG. 5 together. The connector 766 includes an open outlet end 768 carried by a stem structure that extends in a first direction from a bearing plate 777 and is adapted to be sealingly connected to the open inlet end 160 of the filter membrane 170. The connection may be achieved by gluing the open inlet end 160 of the filter membrane 170 to the open outlet end 768 of the connector 766 with, for example, an epoxy resin, a polyurethane resin, a cyanoacrylate resin, a UV curing acrylic adhesive, or a solvent for the material of the hollow connector 766 such as cyclohexanone. In the version depicted, the stem structure of the open outlet end 768 of the connector 766 comprises a hollow cylindrical member that fits inside of and is fixed to the open inlet end 160 of the filter membrane 170. As such, an outer diameter of the open outlet end 768 of the connector 766 is substantially similar to or slightly smaller than an inner diameter of the open inlet end 160 of the filter membrane 170. In some versions, the open inlet end 160 of the filter membrane 170 may be welded to the open outlet end 768 of the connector 766 by, for example, heat welding (e.g., introducing a hot conical metal tip into the open inlet end 150 of the filter membrane 170 to partially melt it), laser welding if the hollow connector 766 is made from a material that absorbs laser radiation, mirror welding, ultrasound welding, and friction welding. Alternately, the filter membrane 170 may be inserted into a mold, and a thermoplastic polymer may be injection-molded around it to form the hollow connector 766. Other designs and configurations for connecting the filter membrane 170 to the connector 766 are intended to be within the scope of the present disclosure.

The hollow connector 766 further includes a fluid inlet 769, which is also a stem structure, extending in a second direction (opposite the first direction) from the bearing plate 777. A pharmaceutical fluid can be fed via a connected fluid supply line, for example, into the fluid inlet 769 of the hollow connector 766. In some versions, the fluid inlet 769 can include a Luer type fitting or other standard medical fitting. The pharmaceutical fluid can then travel through the hollow connector 766 and exit into the filter membrane 170 through the open outlet end 768 of the hollow connector 766.

The hollow connector 766 also includes a sealing surface 772 to which the stem 156 is attached. The sealing surface 772 in this version is a cylindrical shroud extending from the bearing plate 777 in the first direction and has a diameter larger than a diameter of the open outlet end 768. The sealing surface 772 is disposed generally concentric with the open outlet end 768. As such, in this embodiment, the shroud of the sealing surface 772 surrounds the stem structure of the open outlet end 768 such that an annular gap 779 resides between the two. In fact, in this version, the outer diameter of the sealing surface 772 is generally identical to or slightly smaller than an inner diameter of the stem 156. So configured, the sealing surface 772 of the connector 766 can be received by the stem 156 such that the stem 156 extends therefrom to surround and protect the filter membrane 170 without contacting the surface 164 of the filter membrane 170. The stem 156 can be fixed to the sealing surface 772 with adhesive (e.g., a UV curing acrylic adhesive), epoxy, welding, bonding, etc. The stem 156 receives the pharmaceutical fluid after it passes through the pores 162 in the filter membrane 170. From there, the now filtered fluid passes out of the outlet 136 of the stem 156 and to the syringe 102.

While the foregoing version of the filter membrane 170 has been described as including a single filter membrane 170, in other embodiments within the scope of the present disclosure, the filter membrane 170 may include multiple filter membranes 170. A few non-limiting examples of multiple membrane filters will be discussed below.

In one version of the foregoing assembly of FIG. 5, and as mentioned, the stem 156 includes an inner diameter that is larger than an outer diameter of the filter membrane 170, and the stem 156 includes a longitudinal dimension that is larger than a longitudinal dimension of the filter membrane 170. As such, when the stem 156 and filter membrane 170 are assembled onto the connector 166, the filter membrane 170 resides entirely within (i.e., entirely inside of) the stem 156 and a gap exists between the inner sidewall of the stem 156 and the outer sidewall of the filter membrane 170. As such, fluid passing into the filter membrane 170 passes out of the plurality of pores 162 and flows without obstruction through the gap and along the inside of the stem 156. In some versions, the stem 156 can be a flexible tube, a rigid tube, or can include a tube with portions that are flexible and other portions that are rigid. Specifically, in some versions, a stem 156 with at least a rigid portion adjacent to the filter membrane 170 can serve to further protect the filter membrane 170 and/or prevent the filter membrane 170 from becoming pinched or kinked in a flexible tube. In other versions, such protection may not be needed or desirable. In one embodiment, the stem 156 has an internal diameter in the range of approximately 2.5 mm to approximately 8 mm, and a longitudinal dimension in the range of approximately 5 cm to approximately 30 cm. In one embodiment, the internal diameter of the stem 156 is about 0.2 to about 3 mm larger than the outer diameter of the filter membrane 170. And, the filter membrane 170 has an outer diameter in the range of approximately 2.3 mm to approximately 5 mm, a longitudinal dimension in the range of approximately 3 cm to approximately 420 cm, and a wall thickness in the range of approximately 150 μm to approximately 500 μm. Furthermore, in one version each of the plurality of pores 162 in the filter membrane 170 have a diameter less than or equal to approximately 0.2 microns. In some versions, each pore has a diameter less than or equal to a value in a range of approximately 0.1 microns to approximately 0.5 microns, for instance, approximately 0.2 to approximately 0.4 microns. In some versions, each pore has a diameter that is less than or equal to approximately 0.22 microns. In some versions, each pore has a diameter that is less than or equal to a value in a range of approximately 0.1 microns to approximately 0.2 microns. In some versions, each pore has a diameter that is less than or equal to a value in a range of approximately 0.1 microns to approximately 0.22 microns. These pore sizes coupled with the disclosed geometrical dimension of the stem 156 and filter membrane 170 ensure acceptable flow rates through the filter membrane 170 for filling syringes with patient injectable solutions such as sterile water, sterile saline, etc. In other versions, any or all of the dimensions could vary depending on the specific application.

Suitable materials for the filter membrane 170 can include polyolefins (e.g., PE, PP), polyvinylidene fluoride, polymethylmethacrylate, polyacrylonitrile, polysulfone, and polyethersulfone. In some embodiments within the scope of the present disclosure, the filter membrane 170 may be comprised of a blend of polysulfone or polyethersulfone and polyvinylpyrrolidone. In other embodiments within the scope of the present disclosure, the filter membrane 170 can include a polymer containing cationic charges, e.g. polymers bearing functional groups like quaternary ammonium groups. A suitable example for such polymers is polyethyleneimine. The filter membrane 170 may be manufactured by known techniques including, e.g., extrusion, phase inversion, spinning, chemical vapor deposition, 3D printing, etc. Suitable materials for the stem 156 include PVC, polyesters like PET, poly(meth)acrylates like PMMA, polycarbonates (PC), polyolefins like PE, PP, or cycloolefin copolymers (COC), polystyrene (PS), silicone polymers, etc.

Additional details regarding some possible versions of the filter and the specific construction of the membrane, for example, can be found in European Patent Application No. EP16152332.9, entitled FILTER MEMBRANE AND DEVICE, filed Jan. 22, 2016, and additionally in PCT/EP2017/051044, entitled FILTER MEMBRANE AND DEVICE, filed Jan. 19, 2017, the entire contents of each of which are expressly incorporated herein by reference.

Thus far, the hollow fiber membrane 170 in FIG. 5, for example, has been described as being located within the stem 156. In other embodiments, the filter membrane 170 may include its own housing or other support structure, which is coupled to the stem 156 either in place of the connector 166 in FIG. 5 or connector 766 in FIGS. 6-10, or at a location between two portions of the stem 156.

Figure 11:
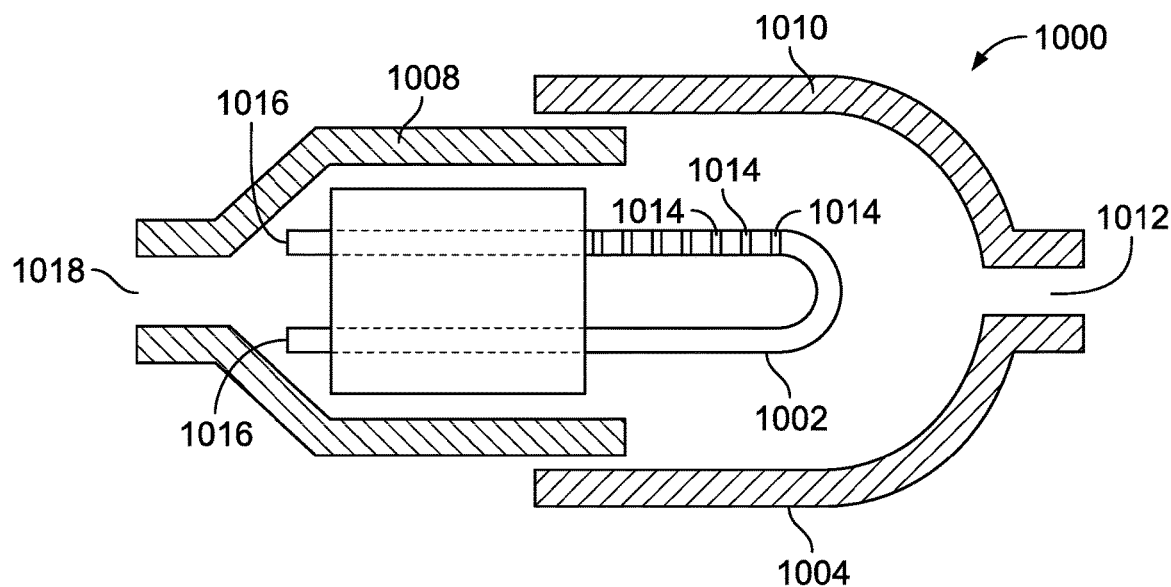
FIG. 11 is a front view of an alternative embodiment of a filtration device having a single looped hollow fiber membrane contained within a filter body for use with the syringe system of the present disclosure.

For example, FIG. 11 is a front view of a filter assembly 1000 for a syinge (not pictured) having a single U-shaped hollow fiber filter membrane 1002 contained within a filter body 1004. The filter membrane 1002 is secured to a filter membrane housing 1006 in the U-shaped configuration with an adhesive (i.e., a UV curing acrylic adhesive), an epoxy, welding, bonding, or other means. The filter membrane housing 1006 is connected to the filter body 1004 at an outlet portion 1008 of the filter body 1004. An inlet portion 1010 is sealably connected to the outlet portion 1008 of the filter body 1004 at a joint or other seam. The inlet portion 1010 of the filter body 1004 has an inlet 1012 by which a pharmaceutical fluid may enter the filter assembly 1000. The pharmaceutical fluid then enters the filter membrane 1002 through a plurality of pores 1014, travels through the filter membrane 1002, exits the filter membrane 1002 at filter membrane outlets 1016, and exits the filter body 1004 at filter outlet 1018. The filter outlet 418 may then be connected to the syringe (not pictured) via the stem 256 of a syringe (not pictured). In FIG. 11, the flow of fluid through the assembly 1000 has been described as moving from the inlet 1012 of the inlet portion 1010 to the outlet 1018 of the outlet portion 1008. However, the same assembly 400 could be used in the opposite direction such that fluid enters the outlet 1018 of the outlet portion 1008 and exits the inlet 1012 of the inlet portion 1010. In this alternative configuration, fluid would first enter the inlet 1018, pass into the filter membrane 1002 at the filter membrane outlets 1016, and exit through the pores 1014 and finally the inlet 1012.

Figure 12:
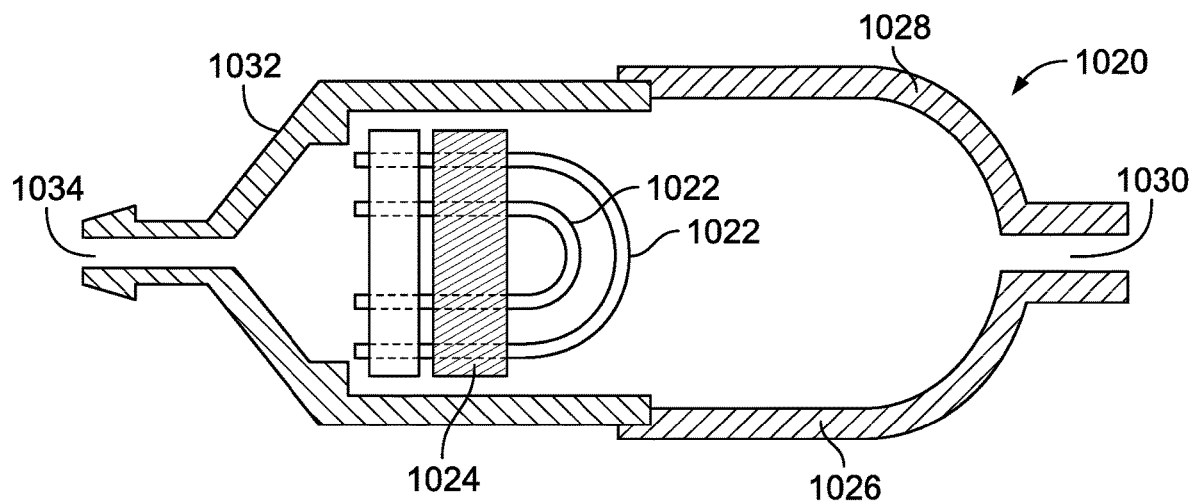
FIG. 12 is a front view of yet another alternative embodiment of a filtration device having a plurality of looped hollow fiber membranes contained within a filter body for use with the syringe system of the present disclosure.

FIG. 12 is an alternate embodiment of the filter assembly 1000 depicted in FIG. 11. In FIG. 12, the filter 1020 includes two U-shaped hollow fiber filter membranes 1022 are secured to a filter membrane housing 1024 in the U-shaped configuration with an adhesive (i.e., a UV curing acrylic adhesive), an epoxy, welding, bonding, or some other means. The filter membranes 1022 and filter membrane housing 1024 are contained within a filter body 1026 having an inlet portion 1028 with inlet 1030 sealably connected to an outlet portion 1032 having filter outlet 1034. In other embodiments, a filter may include more than two U-shaped hollow fiber filter membranes arranged as depicted in FIGS. 11 and 12. In FIG. 12, like in FIG. 11, the flow of fluid through the assembly 1000 has been described as moving from the inlet portion 1028 to the outlet portion 1032. However, the same assembly 1000 could be used in the opposite direction such that fluid enters the outlet portion 1032 and exits the inlet portion 1028 as described above relative to FIG. 11.

Figure 13:
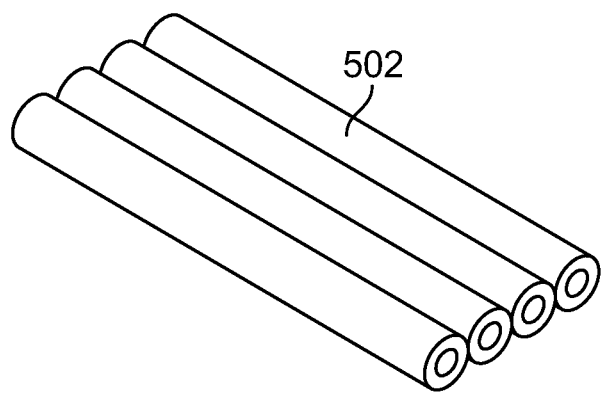
FIG. 13 is a front view of still another embodiment of a filtration device having a plurality of hollow fiber membranes secured side by side for use with the syringe system of the present disclosure.

FIG. 13 is a further alternative filter assembly. Specifically, in FIG. 13, a plurality of linear membrane filters 502 are secured directly together in a parallel side-by-side configuration for what can be referred to as a fiber bundle. The filters 502 in FIG. 13 can be secured together with adhesive (i.e., a UV curing acrylic adhesive), epoxy, welding, bonding, etc. In other versions, the plurality of filters 502 can be manufactured together as one piece by way of any of the manufacturing techniques described above.

Figure 14:
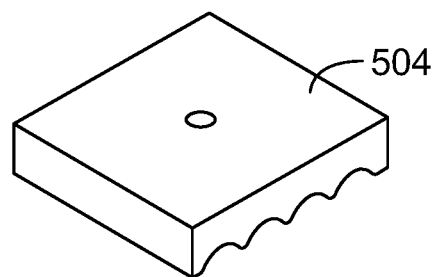
FIG. 14 is an isometric view of the securement device used for the plurality of hollow fiber membranes depicted in FIG. 13.
Figure 14:
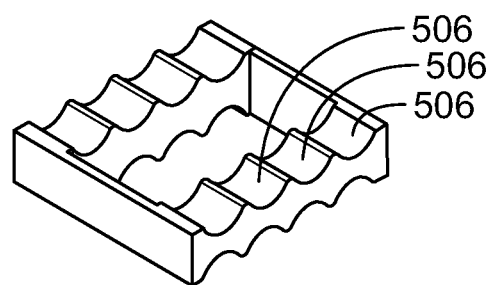
Figure 14:
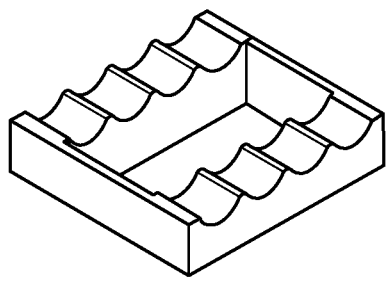

FIG. 14 provides another alternative in which a securement device 504 includes a number of blocks defining a plurality of grooves 506 identical to the number of hollow fiber membrane filters 502. The blocks of the securement device 504 may be sandwiched together and used to hold the plurality of hollow fiber membrane filters 502 in the side-by-side configuration. The securement device 504 depicted in FIG. 14 allows for two sets of the hollow fiber membrane filters 502 of FIG. 13 to be stacked relative to each other. The fiber bundle including the membrane filters 502 and the securement device 504 may be placed in a filter body, such as that discussed with respect to FIGS. 11 and 12.

Figure 15:
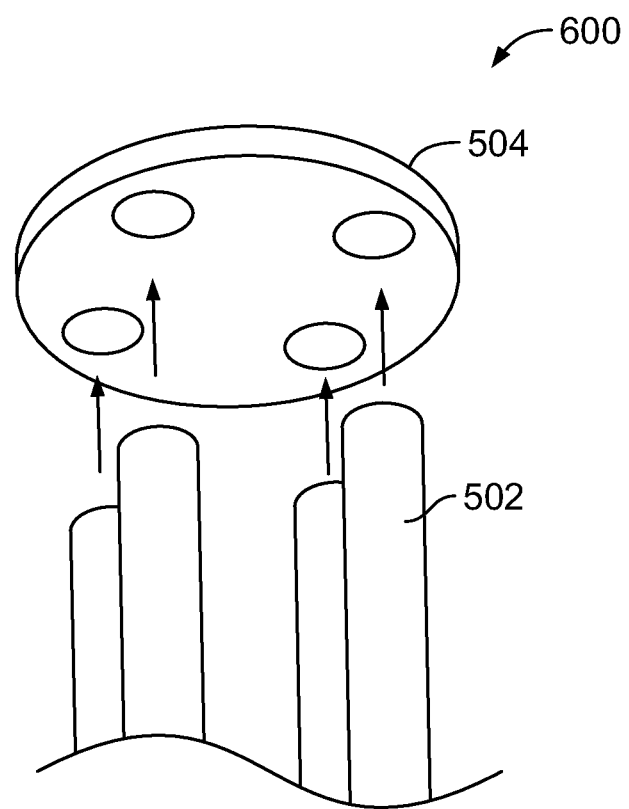
FIG. 15 is an isometric view of still another embodiment of a filtration device having a plurality of hollow fiber membranes secured in a circular holder for use with the syringe system of the present disclosure.

FIG. 15 is an isometric view of another version of a fiber bundle 600 for a syringe (not pictured) having a plurality of parallel hollow fiber membrane filters 502 similar to FIGS. 13 and 14, but wherein the parallel filters 502 are arranged in a circular pattern by a circular holder 504. The fiber bundle 600 may be placed in a filter body, such as that discussed with respect to FIGS. 11 and 12.

Figure 16:
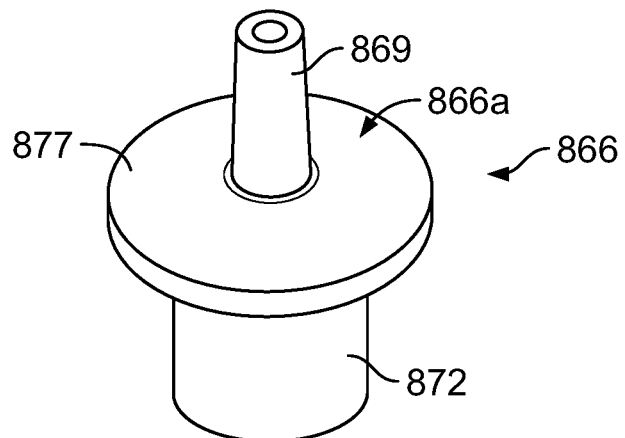
FIG. 16 is an exploded perspective view of an alternative connector for use with a three-filter filter bundle.
Figure 17:
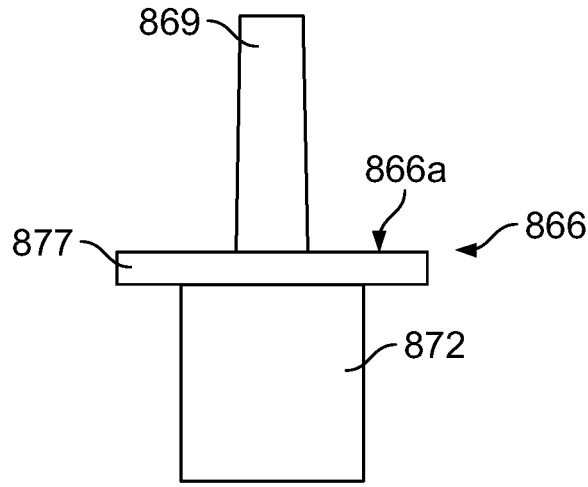
FIG. 17 is a side exploded view of the connector of FIG. 16.
Figure 17:
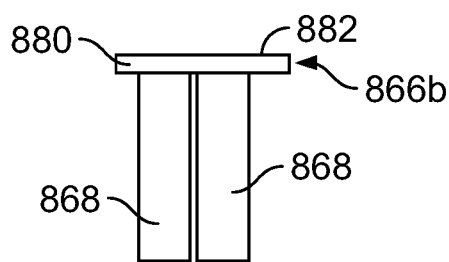

FIGS. 16-17 and FIGS. 18-20 illustrate two additional devices for coupling fiber bundles to a stem in accordance with the present disclosure. FIGS. 16-17 discloses a connector 866 for connecting a three-fiber bundle to a stem. Specifically, the connector 866 includes a first hollow body 866a and a second hollow body 866b. The first body 866a includes a solution inlet 869, which is a stem structure, extending from a bearing plate 877. A pharmaceutical fluid can be fed via a connected fluid supply line, for example, into the fluid inlet 869 of the first hollow body 866a of the connector 866. In some versions, the fluid inlet 869 can include a Luer type fitting or other standard medical fitting.

The hollow connector 866 also includes a sealing surface 872 to which the stem 156 is attached. The sealing surface 872 in this version is a cylindrical shroud extending from the bearing plate 877 in a direction opposite to a direction of extension of the fluid inlet 869. The sealing surface 872 is disposed generally concentric with the fluid inlet 869. As such, in this embodiment, the shroud of the sealing surface 872 defines a cylindrical cavity (not shown in the drawings) for receiving a portion of the second hollow body 866b of the connector 866.

The second hollow body 866b, as depicted, includes a support plate 880 and three open outlet ends 868 extending from the support plate 880. Additionally, the support plate 880 includes an outer diameter that is essentially the same as or slightly smaller than an inner diameter of the cavity of the shroud of the sealing surface 872 such that when assembled, the support plate 880 is positioned into the cavity. In one version, the support plate 880 includes a seal member 882 around its periphery to form a fluid tight seal with the inner surface of the shroud of the sealing surface 872 when inserted into the cavity. Friction, adhesive, or some other means may retain the support plate 880 in connection with the shroud of the sealing surface 872.

As mentioned, the second body 866b includes three open outlet ends 868 extending from the support plate 880. Each open outlet end 868 is adapted to be sealingly connected to an open inlet end 160 of one of three filters 155. The connection may be achieved by gluing open inlet ends 160 of the filters 155 to the open outlet ends 868 with, for example, an epoxy resin, a polyurethane resin, a cyanoacrylate resin, a UV curing acrylic adhesive, or a solvent for the material of the hollow connector 766 such as cyclohexanone. In the version depicted, the stem structure of the open outlet ends 868 of the connector 866 comprises a hollow cylindrical member that fits inside of and is fixed to the open inlet ends 160 of the filters 155. As such, an outer diameter of the open outlet ends 868 is substantially similar to or slightly smaller than an inner diameter of the open inlet ends 160 of the filters 155. In some versions, the filters 155 may be welded to the open outlet ends 868 of the connector 866 by, for example, heat welding (e.g., introducing a hot conical metal tip into the open inlet ends 150 of the filters 155 to partially melt it), laser welding if the hollow connector 866 is made from a material that absorbs laser radiation, mirror welding, ultrasound welding, and friction welding. Alternately, the filters 155 may be inserted into a mold, and a thermoplastic polymer may be injection-molded around it to form the hollow connector 866. Other designs and configurations for connecting the filters 155 to the open outlet ends 868 are intended to be within the scope of the present disclosure.

Finally, as with previously described embodiments, the sealing surface 872 of the connector 866 can be received by the stem 156 such that the stem 156 extends therefrom to surround and protect the filters 155 without contacting the surfaces 164 of the filters 155. The stem 156 can be fixed to the sealing surface 872 with adhesive (e.g., a UV curing acrylic adhesive), epoxy, welding, bonding, etc. The stem 156 receives the pharmaceutical solution after it passes through the pores 162 in the filter membrane 170. From there, the now filtered solution passes out of the outlet 136 of the stem 156.

Figure 18:
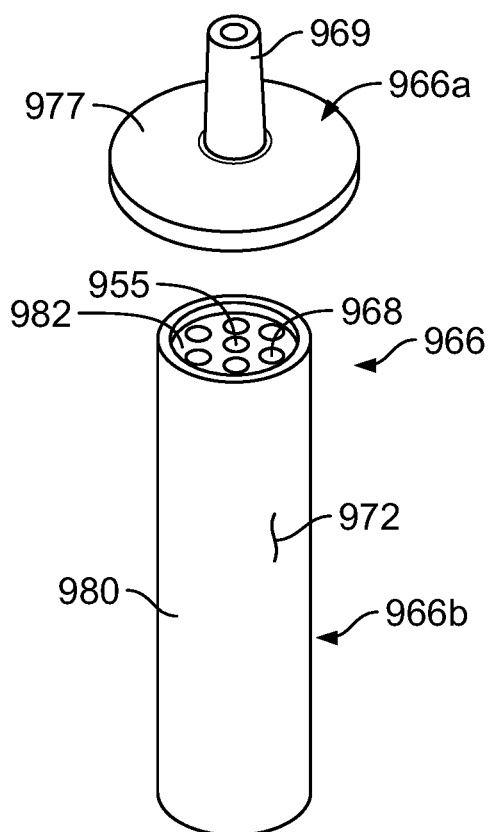
FIG. 18 is a exploded perspective view of another alternative connector for use with a seven-filter filter bundle.
Figure 19:
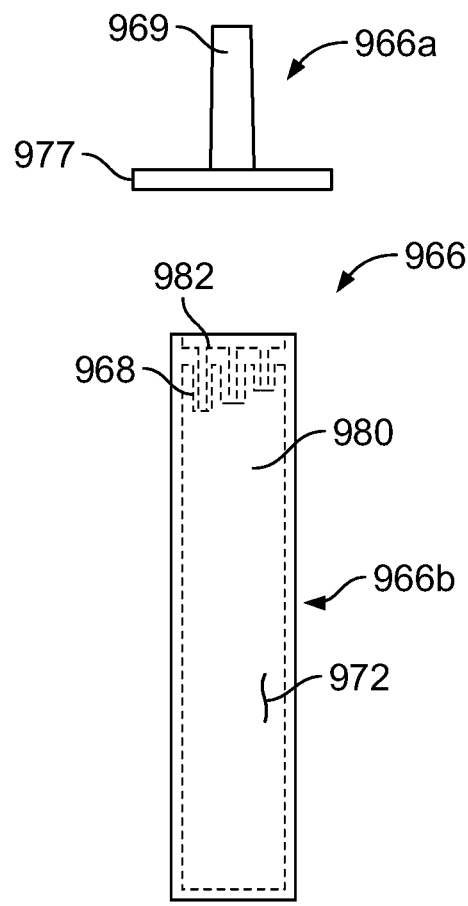
FIG. 19 is a side exploded view of the connector of FIG. 18.
Figure 20:
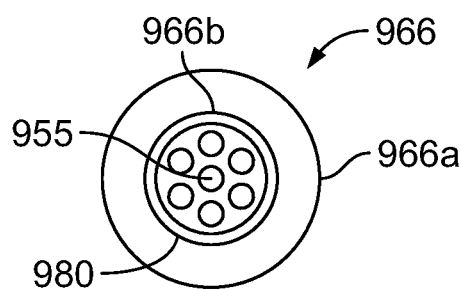
FIG. 20 is a bottom view of the connector of FIG. 19.

FIGS. 18-20 discloses a connector 966 for connecting a seven-fiber bundle to a stem. Specifically, the connector 966 includes a first hollow body 966a and a second hollow body 966b that can be connected to the first hollow body 966a with an adhesive or via other means. The first body 966a includes a solution inlet 969, which is a stem structure, extending from a bearing plate 977. A pharmaceutical fluid can be fed via a connected fluid supply line, for example, into the fluid inlet 969 of the first hollow body 966a of the connector 966. In some versions, the fluid inlet 969 can include a Luer type fitting or other standard medical fitting.

The second hollow body 966b, as depicted, includes a hollow cylindrical support collar 980 in which seven hollow fiber membrane filters 955 can be disposed parallel to each other, as shown in FIGS. 18 and 20. In one version, the support collar 980 can include a support plate 982 carrying seven open outlet ends 968 extending into the collar 980 for connecting to the filters 955 in a manner similar to that described above regarding FIGS. 16-17. The connection may be achieved by gluing the filters 955 to the open outlet ends 968 with, for example, an epoxy resin, a polyurethane resin, a cyanoacrylate resin, a UV curing acrylic adhesive, or a solvent for the material of the hollow connector 966 such as cyclohexanone. In the version depicted, the stem structure of the open outlet ends 868 of the connector 866 comprises a hollow cylindrical member that fits inside of and is fixed to the filters 955. As such, a diameter of the open outlet ends 968 is substantially similar to or slightly smaller than an inner diameter of the filters 955. In some versions, the filters 955 may be welded to the open outlet ends 968 of the connector 966 by, for example, heat welding (e.g., introducing a hot conical metal tip into the filters 955 to partially melt it), laser welding if the hollow connector 966 is made from a material that absorbs laser radiation, mirror welding, ultrasound welding, and friction welding. Alternately, the filters 955 may be inserted into a mold, and a thermoplastic polymer may be injection-molded around it to form the hollow connector 966. Other designs and configurations for connecting the filters 955 to the open outlet ends 968 are intended to be within the scope of the present disclosure.

Finally, the collar 980 of this embodiment includes a sealing surface 972 that can be received by the stem 156 such that the stem 156 extends therefrom. The stem 156 can be fixed to the sealing surface 972 with adhesive (e.g., a UV curing acrylic adhesive), epoxy, welding, bonding, etc. The stem 156 receives the pharmaceutical fluid after it passes through the pores 162 in the filters 955. From there, the now filtered fluid passes out of the outlet 136 of the stem 156.

From the foregoing, it can be seen that various filtering arrangements can serve the principles of the present disclosure including introducing fluid to the syringe system 100 in a sterilized manner. This fluid is then often mixed with a concentrate (e.g., medicament, drug, nutrient, etc.).

While the filtration device 104 throughout the disclosure has been described as including a hollow fiber filter or a plurality of hollow fiber filters, in other versions of the disclosure the filtration device 104 can include other forms of filter assemblies including, for example, a flat filter carried within a housing. The flat filter could have any of the same characteristics as the hollow fiber filter described herein, only its geometrical shape and configuration would be different.

While certain representative versions of the claimed subject matter have been described herein for purposes of illustrating the invention, it will be apparent to those skilled in the art that various changes in the devices and methods disclosed may be made without departing from the spirit and scope of the invention, which is defined by the following claims and is not limited in any manner by the foregoing description.

The invention claimed is:

1. A method of reconstituting a medicinal or nutritional product, the method comprising:
   providing a syringe comprising a syringe barrel having a proximal end defining a barrel opening, a distal end defining a delivery opening, a bore extending between the proximal end and the distal end, a stopper disposed in the bore of the syringe barrel, and a product concentrate disposed in the bore between the stopper and the distal end;
   connecting an outlet of a filtration device to the delivery opening of the syringe barrel, the filtration device comprising a stem and a filter membrane disposed in line with the stem;
   introducing a pharmaceutical fluid into the bore of the syringe barrel through the filter membrane such that a sterilized pharmaceutical fluid can be mixed with the product concentrate in the bore; and
   sealing and cutting the stem of the filtration device at a location between the filter membrane and the distal end of the syringe after introducing the pharmaceutical fluid into the syringe.

2. The method of claim 1, wherein the introducing the pharmaceutical fluid into the bore of the syringe barrel through the filter membrane comprises introducing the pharmaceutical fluid through a plurality of filter membranes.

3. The method of claim 1, wherein the introducing the pharmaceutical fluid into the bore of the syringe barrel through the filter membrane comprises introducing the pharmaceutical fluid through an open outlet end and a sealed outlet end of a hollow fiber of the filter membrane.

4. The method of claim 1, wherein the filter membrane has a wall thickness in the range of approximately 150 μm to approximately 500 μm.

5. The method of claim 1, wherein the filter membrane has a longitudinal dimension in the range of approximately 3 cm to approximately 420 cm, an inner diameter in the range of approximately 2 mm to approximately 4 mm, and an outer diameter in the range of approximately 2.3 mm to approximately 5 mm.

6. The method of claim 1, wherein the introducing the pharmaceutical fluid into the bore of the syringe barrel through the filter membrane comprises introducing the pharmaceutical fluid through a plurality of parallel hollow fiber membrane filters secured in a side-by-side configuration.

7. The method of claim 1, wherein the introducing the pharmaceutical fluid into the bore of the syringe barrel through the filter membrane comprises introducing the pharmaceutical fluid through a plurality of parallel hollow fiber membrane filters arranged in a circular pattern.

8. The method of claim 1, wherein the introducing the pharmaceutical fluid into the bore of the syringe barrel through the filter membrane comprises introducing the pharmaceutical fluid into a second chamber of the bore which is isolated from a first chamber of the bore by a dual-chamber stopper, the second chamber disposed between the dual-chamber stopper and the distal end of the syringe and the first chamber disposed between the dual-chamber stopper and the proximal end of the syringe.

9. The method of claim 8, further comprising introducing the product concentrate into the first chamber of the bore.

10. The method of claim 1, further comprising performing a filter integrity test on the filter membrane after cutting the stem of the filtration device.

11. The method of claim 10, wherein performing the filter integrity test comprises one of a pressure degradation test, a bubble point test, a water intrusion test, or a water flow test.

12. The method of claim 1, wherein the filter membrane has a plurality of pores each with a nominal pore size in a range of approximately 0.1 μm to approximately 0.5 μm.

* * * * *